US011348694B2

(12) United States Patent
Kim et al.

(10) Patent No.: US 11,348,694 B2
(45) Date of Patent: May 31, 2022

(54) MEDICAL ASSESSMENT BASED ON VOICE

(71) Applicant: Canary Speech, LLC, Provo, UT (US)

(72) Inventors: Jangwon Kim, Los Angeles, CA (US); Namhee Kwon, Manhattan Beach, CA (US); Henry O'Connell, Spanish Fork, UT (US); Phillip Walstad, Provo, UT (US); Kevin Shengbin Yang, Boston, MA (US)

(73) Assignee: Canary Speech, Inc., Provo, UT (US)

( * ) Notice: Subject to any disclaimer, the term of this patent is extended or adjusted under 35 U.S.C. 154(b) by 372 days.

(21) Appl. No.: 16/422,718

(22) Filed: May 24, 2019

(65) Prior Publication Data
US 2019/0311815 A1    Oct. 10, 2019

Related U.S. Application Data

(63) Continuation of application No. 15/973,504, filed on May 7, 2018, now Pat. No. 10,311,980.
(Continued)

(51) Int. Cl.
*G16H 80/00* (2018.01)
*G16H 50/20* (2018.01)
(Continued)

(52) U.S. Cl.
CPC .......... *G16H 80/00* (2018.01); *A61B 5/1123* (2013.01); *A61B 5/4088* (2013.01);
(Continued)

(58) Field of Classification Search
CPC ........ G16H 80/00; G16H 10/20; G16H 50/20; G10L 15/22; G10L 15/02; G10L 25/66
See application file for complete search history.

(56) References Cited

U.S. PATENT DOCUMENTS 7,555,431 B2 * 6/2009 Bennett ................. G06F 40/216
704/255
9,763,617 B2    9/2017 Quatieri et al.
(Continued)

FOREIGN PATENT DOCUMENTS

AU         5315699 A  *  2/2000  ............. G01H 1/003
WO      2016028495        2/2016

OTHER PUBLICATIONS

Gonzalez (Gonzalez, Jose et Al. "Direct Speech Reconstruction From Articulatory Sensor Data by Machine Learning." IEEE/ACM Transactions on Audio, Speech and Language Processing, vol. 25, No. 12, Dec. 2017) (Year: 2017).*
(Continued)

*Primary Examiner* — Linh Giang Le
(74) *Attorney, Agent, or Firm* — Kanzler Bean & Adamson, PC

(57) ABSTRACT

Apparatuses, systems, methods, and computer program products are disclosed for medical assessment based on voice. A query module is configured to audibly question a user from a speaker of a mobile computing device with one or more open ended questions. A response module is configured to receive a conversational verbal response of a user from a microphone of a mobile computing device in response to one or more open ended questions. A detection module is configured to provide a machine learning assessment for a user of a medical condition based on a machine learning analysis of a received conversational verbal response of the user.

20 Claims, 12 Drawing Sheets

Related U.S. Application Data

(60) Provisional application No. 62/502,584, filed on May 5, 2017, provisional application No. 62/614,192, filed on Jan. 5, 2018.

(51) Int. Cl.

| | | |
|---|---|---|
| *G10L 25/66* | (2013.01) | |
| *G16H 10/20* | (2018.01) | |
| *A61B 5/11* | (2006.01) | |
| *G06N 20/10* | (2019.01) | |
| *G16H 40/67* | (2018.01) | |
| *G06N 7/00* | (2006.01) | |
| *G16H 50/50* | (2018.01) | |
| *A61B 5/00* | (2006.01) | |
| *G06N 3/08* | (2006.01) | |
| *G10L 15/02* | (2006.01) | |
| *G10L 15/22* | (2006.01) | |
| *G06F 111/10* | (2020.01) | |
| *G10L 15/06* | (2013.01) | |

(52) U.S. Cl.
CPC .......... *A61B 5/4803* (2013.01); *A61B 5/7267* (2013.01); *G06N 3/08* (2013.01); *G06N 7/005* (2013.01); *G06N 20/10* (2019.01); *G10L 25/66* (2013.01); *G16H 10/20* (2018.01); *G16H 40/67* (2018.01); *G16H 50/20* (2018.01); *G16H 50/50* (2018.01); *G06F 2111/10* (2020.01); *G10L 15/02* (2013.01); *G10L 15/063* (2013.01); *G10L 15/22* (2013.01)

(56) References Cited

U.S. PATENT DOCUMENTS

| | | | |
|---|---|---|---|
| 10,152,988 B2 | 12/2018 | Kim et al. | |
| 10,311,980 B2 | 6/2019 | Kim et al. | |
| 10,896,765 B2 | 1/2021 | Kim et al. | |
| 2007/0124135 A1* | 5/2007 | Schultz | G10L 17/26 704/201 |
| 2009/0191521 A1 | 7/2009 | Paul et al. | |
| 2010/0286490 A1 | 11/2010 | Koverzin | |
| 2010/0289490 A1 | 11/2010 | Fan et al. | |
| 2011/0066664 A1* | 3/2011 | Goldman | G06Q 10/10 707/812 |
| 2012/0116186 A1* | 5/2012 | Shrivastav | A61B 5/4803 600/301 |
| 2013/0158434 A1 | 6/2013 | Shen et al. | |
| 2014/0073993 A1 | 3/2014 | Poellabauer | |
| 2014/0365411 A1 | 12/2014 | Beigi et al. | |
| 2015/0073306 A1 | 3/2015 | Abeyratne et al. | |
| 2015/0318002 A1 | 11/2015 | Karam et al. | |
| 2016/0004831 A1 | 1/2016 | Carlson et al. | |
| 2016/0022193 A1 | 1/2016 | Hans et al. | |
| 2017/0053665 A1 | 2/2017 | Quatieri, Jr. et al. | |
| 2017/0076740 A1 | 3/2017 | Feast et al. | |
| 2017/0086672 A1 | 3/2017 | Tran | |
| 2017/0119302 A1 | 5/2017 | Rosenbek et al. | |
| 2017/0125034 A1 | 5/2017 | Kakadiaris et al. | |
| 2017/0249438 A1 | 8/2017 | Jain et al. | |
| 2017/0300648 A1 | 10/2017 | Charlap | |
| 2018/0214061 A1 | 8/2018 | Knoth et al. | |
| 2018/0263496 A1* | 9/2018 | Jiang | A61B 5/163 |
| 2019/0080804 A1 | 3/2019 | Kim et al. | |

OTHER PUBLICATIONS

U.S. Appl. No. 16/189,997 Notice of Allowance and Fees Due, dated Sep. 8, 2020.

EP Patent Application 18794118.2 Search Report, dated Jan. 18, 2021.

EP Patent Application 18794995.7 Search Report, dated Dec. 8, 2020.

U.S. Appl. No. 16/189,997, Office Action, dated Apr. 15, 2020, pp. 1-23.

\* cited by examiner

| Person ID | Diagnosis | Prompt ID | Speech Data |
|---|---|---|---|
| john_smith_123 | Concussion (mild) | concussion1 | 201804121001.wav |
| john_smith_123 | Concussion (mild) | concussion2 | 201804121002.wav |
| john_smith_123 | Concussion (mild) | concussion3 | 201804121003.wav |
| ... | ... | ... | ... |
| jane_doe_456 | Concussion (moderate) | concussion1 | 201804122001.wav |
| jane_doe_456 | Concussion (moderate) | concussion2 | 201804122002.wav |
| jane_doe_456 | Concussion (moderate) | concussion3 | 201804122003.wav |
| ... | ... | ... | ... |

FIG. 3

| Prompt ID | Prompt |
|---|---|
| concussion1 | What venue are we at today? |
| concussion2 | What team did you play last week? |
| concussion3 | Did your team win its last game? |
| ... | ... |
| alzheimers1 | How are you today? |
| alzheimers2 | How many states have you lived in? |
| alzheimers3 | What do you do for a living? |
| ... | ... |

FIG. 4

MEDICAL ASSESSMENT BASED ON VOICE

CROSS-REFERENCES TO RELATED APPLICATIONS

This application is a continuation of U.S. patent application Ser. No. 15/973,504 entitled "MEDICAL ASSESSMENT BASED ON VOICE" and filed on May 7, 2018 for Jangwon Kim, et al. which claims the benefit of U.S. Provisional Patent Application No. 62/502,584 entitled "APPARATUS, SYSTEM, AND METHOD FOR MEDICAL ASSESSMENT BASED ON VOICE" and filed on May 5, 2017 for Megan Davies, et al. and of U.S. Provisional Patent Application No. 62/614,192 entitled "APPARATUS, SYSTEM, AND METHOD FOR VOICE COLLECTION AND MEDICAL ASSESSMENT" and filed on Jan. 5, 2018 for Jangwon Kim, et al., all of which are incorporated herein by reference in their entireties for all purposes.

FIELD

This invention relates to voice analysis and more particularly relates to the automated assessment and diagnosis of one or more medical conditions based on collected voice samples.

BACKGROUND

Assessment of neurological injuries and illnesses and other medical conditions is often performed manually by a medical professional, and can be based on a form filled out by hand with pencil and paper. Manual assessment can be inaccurate and/or inconsistent, and a medical professional may not always be available when injuries or other medical conditions occur.

SUMMARY

Apparatuses are presented for medical assessment based on voice. In one embodiment, a query module is configured to audibly question a user from a speaker of a mobile computing device. A response module, in certain embodiments, is configured to receive a verbal response of a user from a microphone of a mobile computing device. In some embodiments, a detection module is configured to provide an assessment for a user of a medical condition based on an analysis of a received verbal response of the user.

An apparatus, in another embodiment, includes means for audibly questioning a user from a mobile computing device. An apparatus, in certain embodiments, includes means for receiving a verbal response of a user on a mobile computing device. In some embodiments, an apparatus includes means for assessing a user for a medical condition based on a received verbal response of the user.

Systems are presented for medical assessment based on voice. A plurality of distributed voice modules, in certain embodiments, are disposed on computing devices for a plurality of users. In one embodiment, a plurality of distributed voice modules are configured to question a plurality of users and/or to record verbal responses from the plurality of users on computing devices. A backend server device, in various embodiments, is configured to store at least baseline recorded verbal responses from a plurality of users, test case recorded verbal responses from a plurality of users, and/or assessments of a medical condition for at least the test case recorded verbal responses. In one embodiment, a backend server is configured to provide stored baseline recorded verbal responses, test case recorded verbal responses, and/or assessments to at least a subset of a plurality of users on computing devices through a plurality of distributed voice modules.

Methods are presented for medical assessment based on voice. In one embodiment, a method includes querying a user with one or more questions using a user interface of a computing device. A method, in a further embodiment, includes recording, on a computing device, one or more baseline verbal responses of a user to one or more questions. A method, in certain embodiments, includes re-querying a user, in response to a potential concussion event, with one or more questions using a user interface of a computing device. In some embodiments, a method includes recording, on a computing device, one or more test case verbal responses of a user to one or more re-queried questions. A method, in one embodiment, includes assessing, on a computing device, a likelihood that a user has a concussion based on a voice analysis of one or more recorded baseline verbal responses and one or more recorded test case verbal responses.

Computer program products comprising a computer readable storage medium are presented. In certain embodiments, a computer readable storage medium stores computer usable program code executable to perform operations for medical assessment based on voice. In some embodiments, one or more of the operations may be substantially similar to one or more steps described above with regard to the disclosed apparatuses, systems, and/or methods.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 3 is a schematic block diagram illustrating one embodiment of a training corpus of speech data;

FIG. 4 is a schematic block diagram illustrating one embodiment of a list of prompts for using in diagnosing a medical condition;

DETAILED DESCRIPTION

Figure 1A:
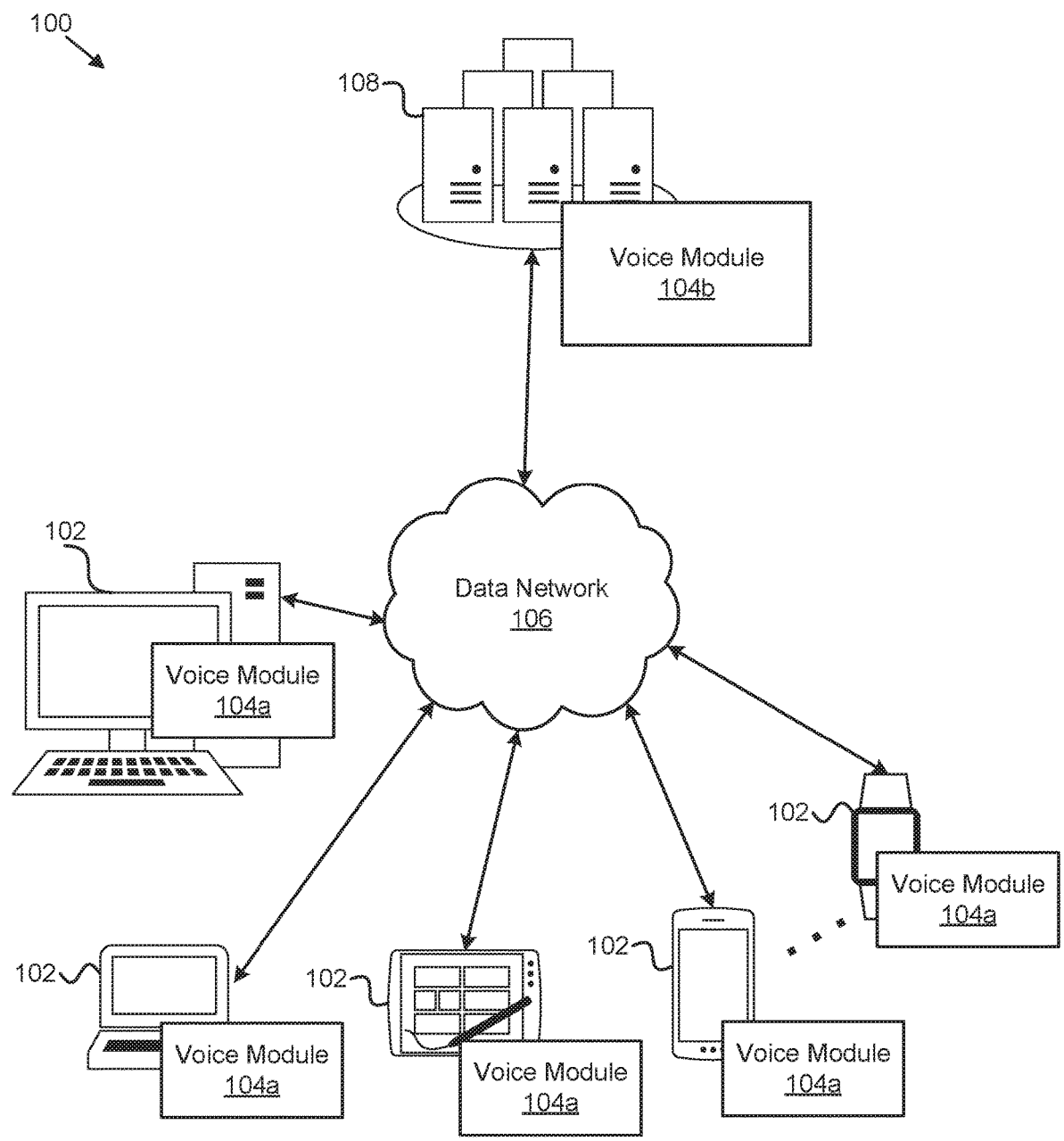
FIG. 1A is a schematic block diagram illustrating one embodiment of a system for medical assessment based on voice.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims, or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules (or components), in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

FIG. 1A depicts one embodiment of a system 100 for voice collection and/or medical assessment based on voice. In one embodiment, the system 100 includes one or more hardware devices 102, one or more voice modules 104 (e.g., one or more voice modules 104a disposed on the one or more hardware devices 102, one or more backend voice modules 104b, or the like), one or more data networks 106 or other communication channels, and/or one or more backend servers 108. In certain embodiments, even though a specific number of hardware devices 102, voice modules 104, data networks 106, and/or backend servers 108 are depicted in FIG. 1, one of skill in the art will recognize, in light of this disclosure, that any number of hardware devices 102, voice modules 104, data networks 106, and/or backend servers 108 may be included in the system 100 for voice collection and/or medical assessment based on voice.

In general, a voice module 104, in various embodiments, is configured to receive and/or record voice audio data from a user (e.g., a patient, an athlete, another user, or the like) and/or to assess and/or diagnose the presence and/or severity of one or more medical conditions (e.g., injuries, illnesses, diseases, or the like) based on collected voice audio data. A voice module 104 may question or query a user (e.g., audibly through a speaker, headphones, or the like; visually with written text on a hardware display device; and/or otherwise using one or more user interface elements of a hardware device 102) to prompt a verbal answer from the user, which the voice module 104 receives and/or records. A voice module 104 may provide an assessment to a user, may provide an assessment and/or voice audio data to a backend voice module 104b, or the like.

A voice module 104 may interact with a user, asking questions verbally, recording the user's vocal responses, determining whether a response is accurate, or the like. For certain protocols, a voice module 104 may ask one or more questions multiple times (e.g., two times, three times, or the like) before moving on to a subsequent question, or the like. Based on the voice audio data, a voice module 104 may assess and/or diagnose one or more diseases or other medical conditions (e.g., concussion, depression, stress, stroke, cognitive well-being, mood, honesty, Alzheimer's disease, Parkinson's disease, cancer, or the like). For example, after audio is captured, a voice module 104 may score responses (e.g., by a device voice module 104*a* on a hardware device 102) and provide the initial one or more scores to a user, and the audio may be further analyzed (e.g., by a backend voice module 104*b* on a server device 108) and a secondary score may be provided to a user with respect to concussion and/or another specific disease or medical condition. A voice module 104 may extract one or more verbal queues and/or features and pass the extracted verbal queues and/or features to one or more machine learning models trained for a certain disease and/or other medical condition.

A voice module 104 may compare a user's answers to previous answers from when the user was healthy (e.g., to baseline answers). A voice module 104 may normalize results based on a user's demographic (e.g., age, gender, or the like). A voice module 104 may determine normalization data as part of training process, determining a range of expected scores for each demographic, or the like.

In certain embodiments, instead of providing an assessment, in addition to providing an assessment, as part of an assessment, or the like, a voice module 104 may assess an efficacy and/or success of a medical trial, a medical drug approval process, or the like. For example, instead of or in addition to a questionnaire for trial participants, which may be subjective, a voice module 104 may objectively assess and/or model changes in a trial participant's voice over the course of the medical trial. For example, a voice module 104 may collect audio from medical trial and/or study participants (e.g., at a doctor's visit, at home, or the like) and may create one or more models for a placebo group and/or for a test group. In some embodiments, a voice module 104 may compare results of a voice assessment and/or model for medical trial and/or study participants with results of a questionnaire or other test, may provide a score similar to and/or on the same scale as a questionnaire or other test, or the like. A voice module 104, in certain embodiments, may provide a voice-based medical assessment to validate a treatment protocol (e.g., a medication and/or another therapeutic treatment) for which there is no known chemical test, to verify and/or validate a chemical test, or the like.

The voice module 104, in certain embodiments, may provide front-end screening of participants in a clinical trial and/or medical study. For example, a voice module 104 may qualify an individual who demonstrates biomarkers in their speech consistent with a depressed individual for a depression study, or the like. Screening participants of a clinical trial and/or medical study using a voice module 104 that identifies biomarkers in their speech may be more objective and/or accurate than using a written questionnaire or similar tool to identify medical trial participants in a subjective manner. Other methods that may achieve objectivity and/or accuracy, such as blood tests, magnetic resonance imaging (Mill) scans, or the like, in certain embodiments, may be more expensive and invasive than a speech analysis by a voice module 104. A voice module 104, in one embodiment, may provide similar objectivity and/or accuracy as other tests, while being noninvasive, having a lower cost, or the like. Identification of medical trial participants using a voice module 104, in one embodiment, is a biomarker data driven, objective tool.

A voice module 104, in some embodiments, may differentiate and/or qualify one or more new drugs (e.g., medications) using behavioral parameters (e.g., behavioral parameters that have been objectively measured and determined to contribute to quality of life, rather than simply approving drugs by their effective morbidity prevention or the like). A voice module 104, in one embodiment, uses vocal biomarkers to identify human conditions (e.g., physical fatigue, tiredness, mental fatigue, stress, anxiety, depression, cognitive impairment, or the like) to measure quality of life and/or one or more other behavioral parameters. Specific conditions and/or behavioral parameters indicating a quality of life may vary based on the medical treatment, the associated medical condition, or the like. For example, an oncology patient may experience "chemo brain" as a side effect of a cancer treatment, and a voice module 104 may detect the patient's impaired cognitive thinking based on an analysis of the patient's voice, indicating the presence of "chemo brain," reducing the patient's quality of life.

For example, a cancer drug therapy may be effective, however, it may be detrimental to the quality of life of the individual using the cancer drug therapy. A patient of a cancer drug therapy may survive, for example, for 5-years after an initial diagnosis, but that 5-years during which the patient is receiving treatment may be miserable due to quality of life changes due to the cancer drug therapy, which may not have not been identified or treated as a result of the drug therapy not having been qualified by a voice module 104, or the like. In the example, a new drug therapy being tested may have similar, or even slightly lower effectiveness, but a much higher quality of life, but would not get approved or otherwise selected for use unless quality of life is also measured by a voice module 104 and considered as a factor in the drug trial and/or medical study.

Instead of subjectively measuring the quality of life and/or behavioral consequences of receiving treatment or drugs using a questionnaire or similar tool, in certain embodiments, a voice module 104 may identify one or more quality of life changes in a patient objectively using biomarkers or other indicators in voice data from the patient. Identification of quality of life and/or other behavioral parameters related to drug or cancer treatment using a voice module 104, in one embodiment, is a biomarker data driven, objective tool. As described in greater detail below, a voice module 104 may assess a quality of life, a medical condition, or the like based on an analysis of a user's responses to one or more prompts. For example, in the "chemo brain" example described above, a voice module 104 may provide a user with a series of prompts selected to assess a current state of one or more symptoms associated with "chemo brain", such as memory loss. To monitor memory loss, in certain embodiments, a voice module 104 may audibly list words and/or numbers to a user and ask the user to repeat them back, may display a series of pictures to the user and ask the user to repeat back a description of the series of pictures, or the like, and monitor changes in an accuracy of the user's responses over time, indicating memory loss and a decreased quality of life.

In one embodiment, the system 100 includes one or more hardware devices 102. The hardware devices 102 and/or the one or more backend servers 108 (e.g., computing devices, information handling devices, or the like) may include one or more of a desktop computer, a laptop computer, a mobile device, a tablet computer, a smart phone, a set-top box, a gaming console, a smart TV, a smart watch, a fitness band, an optical head-mounted display (e.g., a virtual reality headset, smart glasses, or the like), an HDMI or other electronic display dongle, a personal digital assistant, and/or another computing device comprising a processor (e.g., a central processing unit (CPU), a processor core, a field programmable gate array (FPGA) or other programmable logic, an application specific integrated circuit (ASIC), a controller, a microcontroller, and/or another semiconductor integrated circuit device), a volatile memory, and/or a non-volatile storage medium. In certain embodiments, the hardware devices 102 are in communication with one or more backend servers 108 via a data network 106, described below. The hardware devices 102, in a further embodiment, are capable of executing various programs, program code, applications, instructions, functions, or the like.

In various embodiments, a voice module 104 may be embodied as hardware, software, or some combination of hardware and software. In one embodiment, a voice module 104 may comprise executable program code stored on a non-transitory computer readable storage medium for execution on a processor of a hardware device 102; a backend server 108; or the like. For example, a voice module 104 may be embodied as executable program code executing on one or more of a hardware device 102; a backend server 108; a combination of one or more of the foregoing; or the like. In such an embodiment, the various modules that perform the operations of a voice module 104, as described below, may be located on a hardware device 102; a backend server 108; a combination of the two; and/or the like.

In various embodiments, a voice module 104 may be embodied as a hardware appliance that can be installed or deployed on a backend server 108, on a user's hardware device 102 (e.g., a dongle, a protective case for a phone 102 or tablet 102 that includes one or more semiconductor integrated circuit devices within the case in communication with the phone 102 or tablet 102 wirelessly and/or over a data port such as USB or a proprietary communications port, or another peripheral device), or elsewhere on the data network 106 and/or collocated with a user's hardware device 102. In certain embodiments, a voice module 104 may comprise a hardware device such as a secure hardware dongle or other hardware appliance device (e.g., a set-top box, a network appliance, or the like) that attaches to another hardware device 102, such as a laptop computer, a server, a tablet computer, a smart phone, or the like, either by a wired connection (e.g., a USB connection) or a wireless connection (e.g., Bluetooth®, Wi-Fi®, near-field communication (NFC), or the like); that attaches to an electronic display device (e.g., a television or monitor using an HDMI port, a DisplayPort port, a Mini DisplayPort port, VGA port, DVI port, or the like); that operates substantially independently on a data network 106; or the like. A hardware appliance of a voice module 104 may comprise a power interface, a wired and/or wireless network interface, a graphical interface (e.g., a graphics card and/or GPU with one or more display ports) that outputs to a display device, and/or a semiconductor integrated circuit device as described below, configured to perform the functions described herein with regard to a voice module 104.

A voice module 104, in such an embodiment, may comprise a semiconductor integrated circuit device (e.g., one or more chips, die, or other discrete logic hardware), or the like, such as a field-programmable gate array (FPGA) or other programmable logic, firmware for an FPGA or other programmable logic, microcode for execution on a microcontroller, an application-specific integrated circuit (ASIC), a processor, a processor core, or the like. In one embodiment, a voice module 104 may be mounted on a printed circuit board with one or more electrical lines or connections (e.g., to volatile memory, a non-volatile storage medium, a network interface, a peripheral device, a graphical/display interface. The hardware appliance may include one or more pins, pads, or other electrical connections configured to send and receive data (e.g., in communication with one or more electrical lines of a printed circuit board or the like), and one or more hardware circuits and/or other electrical circuits configured to perform various functions of a voice module 104.

The semiconductor integrated circuit device or other hardware appliance of a voice module 104, in certain embodiments, comprises and/or is communicatively coupled to one or more volatile memory media, which may include but is not limited to: random access memory (RAM), dynamic RAM (DRAM), cache, or the like. In one embodiment, the semiconductor integrated circuit device or other hardware appliance of a voice module 104 comprises and/or is communicatively coupled to one or more non-volatile memory media, which may include but is not limited to: NAND flash memory, NOR flash memory, nano random access memory (nano RAM or NRAM), nanocrystal wire-based memory, silicon-oxide based sub-10 nanometer process memory, graphene memory, Silicon-Oxide-Nitride-Oxide-Silicon (SONOS), resistive RAM (RRAM), programmable metallization cell (PMC), conductive-bridging RAM (CBRAM), magneto-resistive RAM (MRAM), dynamic RAM (DRAM), phase change RAM (PRAM or PCM), magnetic storage media (e.g., hard disk, tape), optical storage media, or the like.

The data network 106, in one embodiment, includes a digital communication network that transmits digital communications. The data network 106 may include a wireless network, such as a wireless cellular network, a local wireless network, such as a Wi-Fi network, a Bluetooth® network, a near-field communication (NFC) network, an ad hoc network, and/or the like. The data network 106 may include a wide area network (WAN), a storage area network (SAN), a local area network (LAN), an optical fiber network, the internet, or other digital communication network. The data network 106 may include two or more networks. The data network 106 may include one or more servers, routers, switches, and/or other networking equipment. The data network 106 may also include one or more computer readable storage media, such as a hard disk drive, an optical drive, non-volatile memory, RAM, or the like.

The one or more backend servers 108, in one embodiment, may include one or more network accessible computing systems such as one or more web servers hosting one or more web sites, an enterprise intranet system, an application server, an application programming interface (API) server, an authentication server, or the like. A backend server 108 may include one or more servers located remotely from the hardware devices 102. A backend server 108 may include at least a portion of the voice modules 104, may comprise hardware of a voice module 104, may store executable program code of a voice module 104 in one or more non-transitory computer readable storage media, and/or may otherwise perform one or more of the various operations of a voice module 104 described herein for shared content tracking and attribution.

Figure 1B:
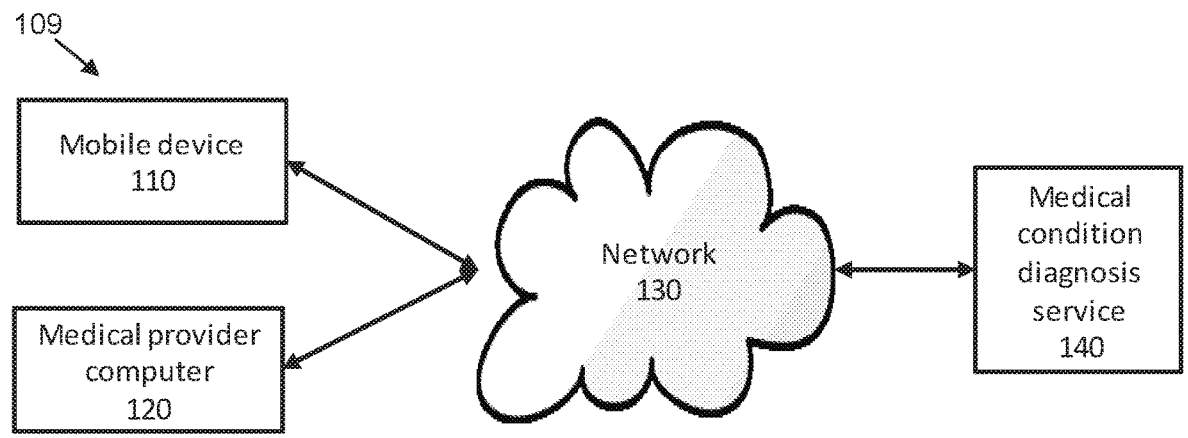
FIG. 1B is a schematic block diagram illustrating a further embodiment of a system for medical assessment based on voice.

FIG. 1B is an example system 109 for diagnosing a medical condition using a person's speech. FIG. 1B includes a medical condition diagnosis service 140 that may receive speech data of a person and process the speech data to determine if a person has a medical condition. For example, medical condition diagnosis service 140 may process the speech data to compute a yes or no determination as to whether the person has the medical condition or to compute a score that indicates a probability or a likelihood that the person has the medical condition and/or a severity of the condition.

As used herein, a diagnosis relates to any determination as to whether a person may have a medical condition or any determination as to a possible severity of the medical condition. A diagnosis may include any form of an assessment, conclusion, opinion, or determination relating to a medical condition. In some instances, a diagnosis may be incorrect, and a person diagnosed with a medical condition may not actually have the medical condition.

Medical condition diagnosis service 140 may receive the speech data of a person using any appropriate techniques. For example, a person may speak to a mobile device 110 and mobile device 110 may record the speech and transmit the recorded speech data to medical condition diagnosis service 140 over network 130. Any appropriate techniques and any appropriate network may be used for mobile device 110 to transmit the recorded speech data to medical condition diagnosis service 140. For example, an application or "app" may be installed on mobile device 110 that uses a REST (representational state transfer) API (application programming interface) call to transmit the speech data over the Internet or a mobile telephone network. In another example, a medical provider may have a medical provider computer 120 that is used to record speech of a person and transmit speech data to medical condition diagnosis service 140.

In some implementations, medical condition diagnosis service 140 may be installed on mobile device 110 or medical provider computer 120 such that it is not necessary to transmit the speech data over a network. The example of FIG. 1B is not limiting, and any appropriate techniques may be used to transmit speech data for processing by a mathematical model.

The output of medical condition diagnosis service 140 may then be used for any appropriate purpose. For example, information may be presented to the person who provided the speech data or to a medical professional who is treating the person.

Figure 2:
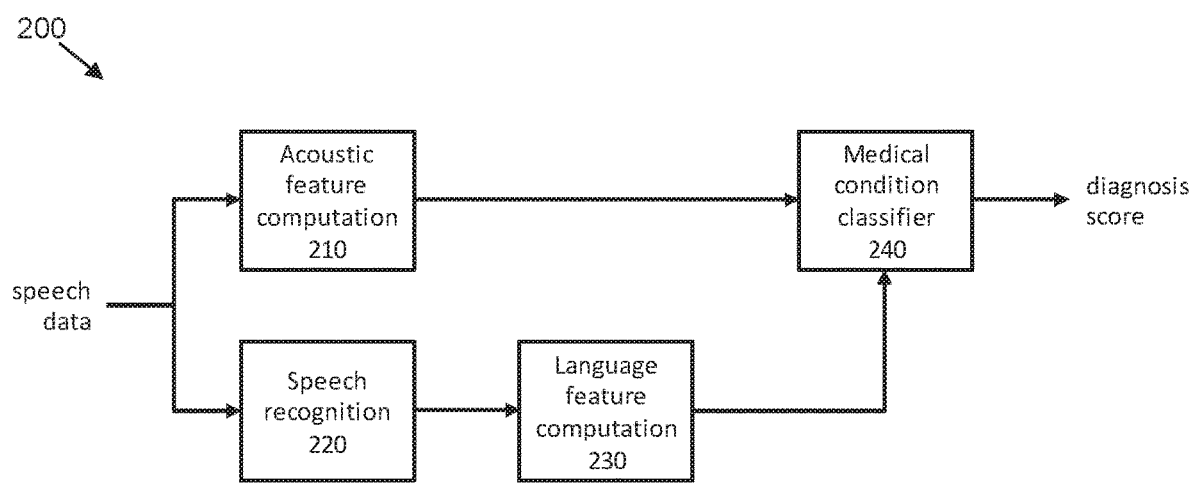
FIG. 2 is a schematic block diagram illustrating one embodiment of a system for processing speech data with a mathematical model to perform a medical diagnosis.

FIG. 2 is an example system 200 for processing speech data with a mathematical model to perform a medical diagnosis. In processing the speech data, features may be computed from the speech data, and then the features may be processed by the mathematical model. Any appropriate type of features may be used.

The features may include acoustic features, where acoustic features are any features computed from the speech data that do not involve or depend on performing speech recognition on the speech data (e.g., the acoustic features do not use information about the words spoken in the speech data). For example, acoustic features may include mel-frequency cepstral coefficients, perceptual linear prediction features, jitter, or shimmer.

The features may include language features where language features are computed using the results of a speech recognition. For example, language features may include a speaking rate (e.g., the number of vowels or syllables per second), a number of pause fillers (e.g., "ums" and "ahs"), the difficulty of words (e.g., less common words), or the parts of speech of words following pause fillers.

In FIG. 2, the speech data is processed by acoustic feature computation component 210 and speech recognition component 220. Acoustic feature computation component 210 may compute acoustic features from the speech data, such as any of the acoustic features described herein. Speech recognition component 220 may perform automatic speech recognition on the speech data using any appropriate techniques (e.g., Gaussian mixture models, acoustic modelling, language modelling, and neural networks).

Because speech recognition component 220 may use acoustic features in performing speech recognition, some processing of these two components may overlap and thus other configurations are possible. For example, acoustic feature component 210 may compute the acoustic features needed by speech recognition component 220, and speech recognition component 220 may thus not need to compute any acoustic features.

Language feature computation component 230 may receive speech recognition results from speech recognition component 220, and process the speech recognition results to determine language features, such as any of the language features described herein. The speech recognition results may be in any appropriate format and include any appropriate information. For example, the speech recognition results may include a word lattice that includes multiple possible sequences of words, information about pause fillers, and the timings of words, syllables, vowels, pause fillers, or any other unit of speech.

Medical condition classifier 240 may process the acoustic features and the language features with a mathematical model to output one or more diagnosis scores that indicate whether the person has the medical condition, such as a score indicating a probability or likelihood that the person has the medical condition and/or a score indicating a severity of the medical condition. Medical condition classifier 240 may use any appropriate techniques, such as a classifier implemented with a support vector machine or a neural network, such as a multi-layer perceptron.

The performance of medical condition classifier 240 may depend on the features computed by acoustic feature computation component 210 and language feature computation component 230. Further, a set of features that performs well for one medical condition may not perform well for another medical condition. For example, word difficulty may be an important feature for diagnosing Alzheimer's disease but may not be useful for determining if a person has a concussion. For another example, features relating to the pronunciation of vowels, syllables, or words may be important for Parkinson's disease but may be less important for other medical conditions. Accordingly, techniques are needed for determining a first set of features that performs well for a first medical condition, and this process may need to be repeated for determining a second set of features that performs well for a second medical condition.

In some implementations, medical condition classifier 240 may use other features, which may be referred to as non-speech features, in addition to acoustic features and language features. For example, features may be obtained or computed from demographic information of a person (e.g., gender, age, or place of residence), information from a medical history (e.g., weight, recent blood pressure readings, or previous diagnoses), or any other appropriate information.

The selection of features for diagnosing a medical condition may be more important in situations where an amount of training data for training the mathematical model is relatively small. For example, for training a mathematical model for diagnosing concussions, the needed training data may include speech data of a number of individuals shortly after they experience a concussion. Such data may exist in small quantities and obtaining further examples of such data may take a significant period of time.

Training mathematical models with a smaller amount of training data may result in overfitting where the mathematical model is adapted to the specific training data but because of the small amount of training data, the model may not perform well on new data. For example, the model may be able to detect all of the concussions in the training data, but may have a high error rate when processing production data of people who may have concussions.

One technique for preventing overfitting when training a mathematical model is to reduce the number of features used to train the mathematical model. The amount of training data needed to train a model without overfitting increases as the number of features increases. Accordingly, using a smaller number of features allows models to be built with a smaller amount of training data.

Where it is needed to train a model with a smaller number of features, it becomes more important to select the features that will allow the model to perform well. For example, when a large amount of training data is available, hundreds of features may be used to train the model and it is more likely that appropriate features have been used. Conversely, where a small amount of training data is available, only 10 or so features may be used to train a model, and it is more important to select the features that are most important for diagnosing the medical condition.

Now presented are examples of features that may be used to diagnose a medical condition.

Acoustic features may be computed using short-time segment features. When processing speech data, the duration of the speech data may vary. For example, some speech may be a second or two and other speech may be several minutes or more. For consistency in processing speech data, it may be processed in short-time segments (sometimes referred to as frames). For example, each short-time segment may be 25 milliseconds, and segments may advance in increments of 10 milliseconds so that there is a 15 millisecond overlap over two successive segments.

The following are non-limiting examples of short-time segment features: spectral features (such as mel-frequency cepstral coefficients or perceptual linear predictives); prosodic features (such as pitch, energy, or probability of voicing); voice quality features (such as jitter, jitter of jitter, shimmer, or harmonics-to-noise ratio); entropy (e.g., to capture how precisely an utterance is pronounced where entropy may be computed from the posteriors of an acoustic model that is trained on natural speech data).

The short-time segment features may be combined to compute acoustic features for the speech. For example, a two-second speech sample may produce 200 short-time segment features for pitch that may be combined to compute one or more acoustic features for pitch.

The short-time segment features may be combined to compute an acoustic feature for a speech sample using any appropriate techniques. In some implementations, an acoustic feature may be computed using statistics of the short-time segment features (e.g., arithmetic mean, standard deviation, skewness, kurtosis, first quartile, second quartile, third quartile, the second quartile minus the first quartile, the third quartile minus the first quartile, the third quartile minus the second quartile, 0.01 percentile, 0.99 percentile, the 0.99 percentile minus the 0.01 percentile, the percentage of short-time segments whose values are above a threshold (e.g., where the threshold is 75% of the range plus the minimum), the percentage of segments whose values are above a threshold (e.g., where the threshold is 90% of the range plus the minimum), the slope of a linear approximation of the values, the offset of a linear approximation of the values, the linear error computed as the difference of the linear approximation and the actual values, or the quadratic error computed as the difference of the linear approximation and the actual values. In some implementations, an acoustic feature may be computed as an i-vector or identity vector of the short-time segment features. An identity vector may be computed using any appropriate techniques, such as performing a matrix-to-vector conversion using a factor analysis technique and a Gaussian mixture model.

The following are non-limiting examples of language features. A speaking rate, such as by computing the duration of all spoken words divided by the number of vowels or any other appropriate measure of speaking rate. A number of pause fillers that may indicate hesitation in speech, such as (1) a number of pause fillers divided by the duration of spoken words or (2) a number of pause fillers divided by the number of spoken words. A measure of word difficulty or the use of less common words. For example, word difficulty may be computed using statistics of 1-gram probabilities of the spoken words, such as by classifying words according to their frequency percentiles (e.g., 5%, 10%, 15%, 20%, 30%, or 40%). The parts of speech of words following pause fillers, such as (1) the counts of each part-of-speech class divided by the number of spoken words or (2) the counts of each part-of-speech class divided by the sum of all part-of-speech counts.

In some implementations, language features may include a determination of whether a person answered a question correctly. For example, a person may be asked what the current year is or who the President of the United States is. The person's speech may be processed to determine what the person said in response to the question and to determine if the person answered the question correctly.

To train a model for diagnosing a medical condition, a corpus of training data may be collected. The training corpus may include examples of speech where the diagnosis of the person is known. For example, it may be known that the person had no concussion, or a mild, moderate, or severe concussion.

FIG. 3 illustrates an example of a training corpus that includes speech data for training a model for diagnosing concussions. For example, the rows of the table of FIG. 3 may correspond to database entries. In this example, each entry includes an identifier of a person, the known diagnosis of the person (e.g., no concussion or a mild, medium, or severe concussion), an identifier of a prompt or question that was presented to a person (e.g., "How are you today?"), and a filename of a file that contains the speech data. The training data may be stored in any appropriate format using any appropriate storage technology.

The training corpus may store a representation of a person's speech using any appropriate format. For example, a speech data item of the training corpus may include digital samples of an audio signal received at a microphone or may include a processed version of the audio signal, such as mel-frequency cepstral coefficients.

A single training corpus may contain speech data relating to multiple medical conditions, or a separate training corpus may be used for each medical condition (e.g., a first training corpus for concussions and a second training corpus for Alzheimer's disease). A separate training corpus may be used for storing speech data for people with no known or diagnosed medical condition, as this training corpus may be used for training models for multiple medical conditions.

FIG. 4 illustrates an example of stored prompts that may be used to diagnose medical conditions. Each prompt may be presented to a person, either by a person (e.g., a medical professional) or a computer, to obtain speech of the person in response to the prompt. Each prompt may have a prompt identifier so that it may be cross referenced with the prompt identifier of the training corpus. The prompts of FIG. 4 may be stored using any appropriate storage technology, such as a database.

Figure 5:
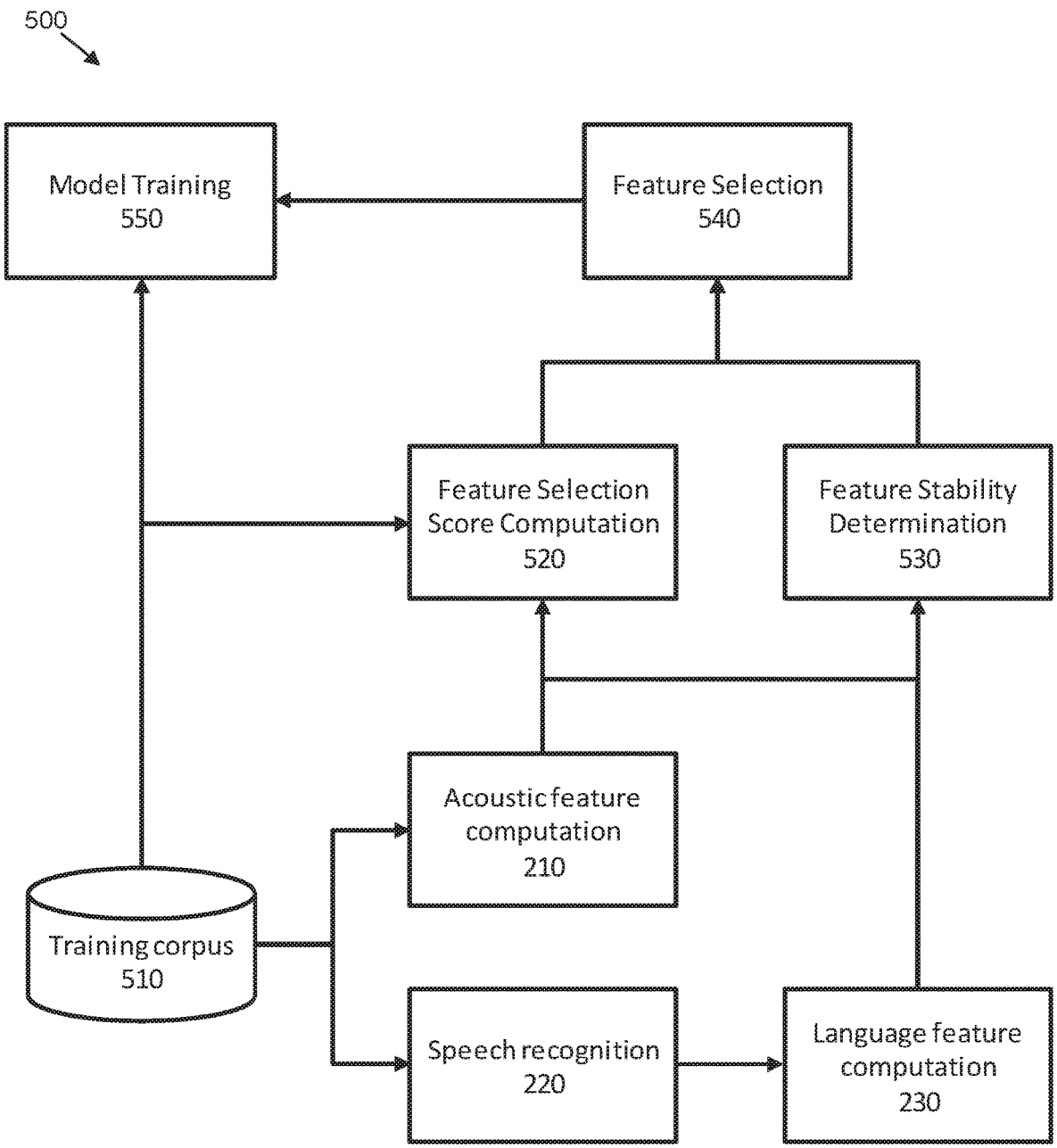
FIG. 5 is a schematic block diagram illustrating one embodiment of a system for selecting features for training a mathematical model for diagnosing a medical condition.

FIG. 5 is an exemplary system 500 that may be used to select features for training a mathematical model for diagnosing a medical condition, and then using the selected features to train the mathematical model. System 500 may be used multiple times to select features for different medical conditions. For example, a first use of system 500 may select features for diagnosing concussions and a second use of system 500 may select features for diagnosing Alzheimer's disease.

FIG. 5 includes a training corpus 510 of speech data items for training a mathematical model for diagnosing a medical condition. Training corpus 510 may include any appropriate information, such as speech data of multiple people with and without the medical condition, a label indicating whether or not person has the medical condition, and any other information described herein.

Acoustic feature computation component 210, speech recognition component 220, and language feature computation component 230 may be implemented as described above to compute acoustic and language features for the speech data in the training corpus. Acoustic feature computation component 210 and language feature computation component 230 may compute a large number of features so that the best performing features may be determined. This may be in contrast to FIG. 2 where these components are used in a production system and thus these components may compute only the features that were previously selected.

Feature selection score computation component 520 may compute a selection score for each feature (which may be an acoustic feature, a language feature, or any other feature described herein). To compute a selection score for a feature, a pair of numbers may be created for each speech data item in the training corpus, where the first number of the pair is the value of the feature and the second number of the pair is an indicator of the medical condition diagnosis. The value for the indicator of the medical condition diagnosis may have two values (e.g., 0 if the person does not have the medical condition and 1 if the person has the medical condition) or may have a larger number of values (e.g., a real number between 0 and 1 or multiple integers indicating a likelihood or severity of the medical condition).

Figure 6A:
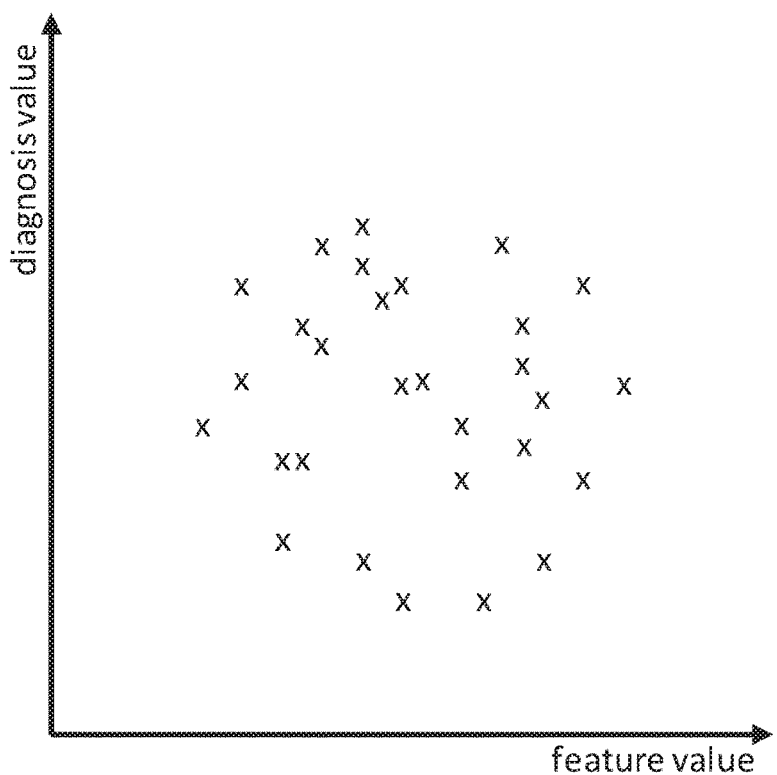
FIG. 6A is a schematic block diagram illustrating one embodiment of a graph of pairs of feature values and diagnosis values.
Figure 6B:
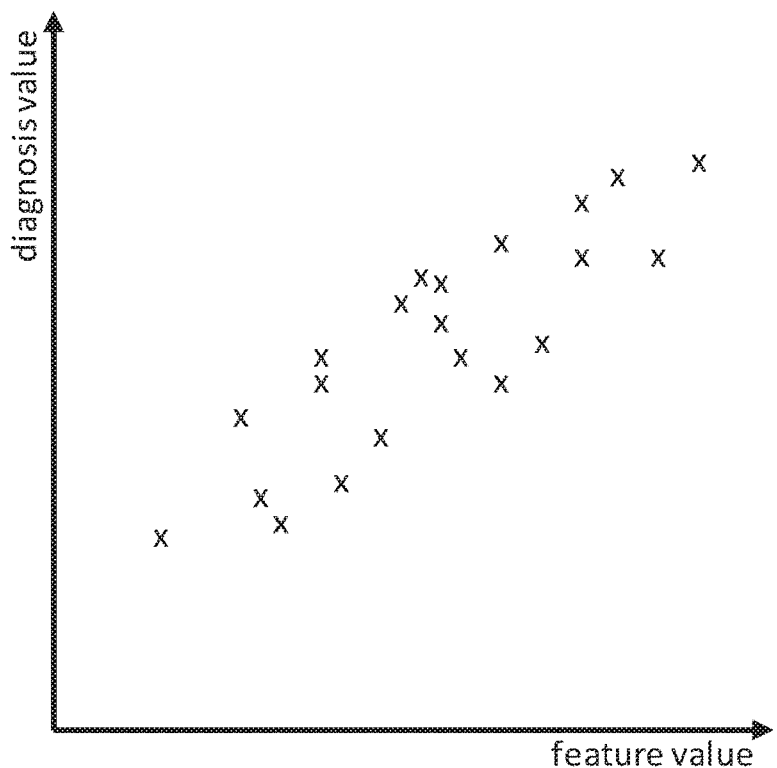
FIG. 6B is a schematic block diagram illustrating a further embodiment of a graph of pairs of feature values and diagnosis values.

Accordingly, for each feature, a pair of numbers may be obtained for each speech data item of the training corpus. FIGS. 6A and 6B illustrate two conceptual plots of the pairs of numbers for a first feature and a second feature. For FIG. 6A, there does not appear to be a pattern or correlation between the values of the first feature and the corresponding diagnosis values, but for FIG. 6B, there does appear to be a pattern or correlation between the values of the second feature and the diagnosis values. Accordingly, one may conclude that the second feature is likely a useful feature for determining whether a person has the medical condition and that the first feature is not.

Feature selection score computation component 520 may compute a selection score for a feature using the pairs of feature values and diagnosis values. Feature selection score computation component 520 may compute any appropriate score that indicates a pattern or correlation between the feature values and the diagnosis values. For example, feature selection score computation component 520 may compute a Rand index, an adjusted Rand index, mutual information, adjusted mutual information, a Pearson correlation, an absolute Pearson correlation, a Spearman correlation, or an absolute Spearman correlation.

The selection score may indicate the usefulness of the feature in detecting a medical condition. For example, a high selection score may indicate that a feature should be used in training the mathematical model, and a low selection score may indicate that the feature should not be used in training the mathematical model.

Feature stability determination component 530 may determine if a feature (which may be an acoustic feature, a language feature, or any other feature described herein) is stable or unstable. To make a stability determination, the speech data items may be divided into multiple groups, which may be referred to as folds. For example, the speech data items may be divided into five folds. In some implementations, the speech data items may be divided into folds such that each fold has an approximately equal number of speech data items for different genders and age groups.

The statistics of each fold may be compared to statistics of the other folds. For example, for a first fold, the median (or mean or any other statistic relating to the center or middle of a distribution) feature value (denoted as $M_1$) may be determined. Statistics may also be computed for the combination of the other folds. For example, for the combination of the other folds, the median of the feature values (denoted as $M_o$) and a statistic measuring of variability of the feature values (denoted as $V_o$), such as interquartile range, variance, or standard deviation, may be computed. The feature may be determined to be unstable if the median of the first fold differs too greatly from the median of the second fold. For example, the feature may be determined to be unstable if $$M_1 < M_o - C\frac{V_o}{2} \text{ or } M_1 > M_o + C\frac{V_o}{2}$$

where C is a scaling factor. The process may then be repeated for each of the other folds. For example, the median of a second fold may be compared with median and variability of the other folds as described above.

In some implementations, if, after comparing each fold to the other folds, the median of each fold is not too far from the median of the other folds, then the feature may be determined to be stable. Conversely, if the median of any fold is too far from the median of the other folds, then the feature may be determined to be unstable.

In some implementations, feature stability determination component 530 may output a Boolean value for each feature to indicate whether the feature is stable or not. In some implementations, stability determination component 530 may output a stability score for each feature. For example, a stability score may be computed as largest distance between the median of a fold and the other folds (e.g., a Mahalanobis distance).

Feature selection component 540 may receive the selection scores from feature selection score computation component 520 and the stability determinations from feature stability determination component 530 and select a subset of features to be used to train the mathematical model. Feature selection component 540 may select a number of features having the highest selection scores that are also sufficiently stable.

In some implementations, the number of features to be selected (or a maximum number of features to be selected) may be set ahead of time. For example, a number N may be determined based on the amount of training data, and N features may be selected. The selected features may be determined by removing unstable features (e.g., features determined to be unstable or features with a stability score below a threshold) and then selecting the N features with the highest selection scores.

In some implementations, the number of features to be selected may be based on the selection scores and stability determinations. For example, the selected features may be determined by removing unstable features, and then selecting all features with a selection score above a threshold.

In some implementations, the selection scores and stability scores may be combined when selecting features. For example, for each feature a combined score may be computed (such as by adding or multiplying the selection score and the stability score for the feature) and features may be selected using the combined score.

Model training component 550 may then train a mathematical model using the selected features. For example, model training component 550 may iterate over the speech data items of the training corpus, obtain the selected features for the speech data items, and then train the mathematical model using the selected features. In some implementations, dimension reduction techniques, such as principal components analysis or linear discriminant analysis, may be applied to the selected features as part of the model training. Any appropriate mathematical model may be trained, such as any of the mathematical models described herein.

In some implementations, other techniques, such as wrapper methods, may be used for feature selection or may be used in combination with the feature selection techniques presented above. Wrapper methods may select a set of features, train a mathematical model using the selected set of features, and then evaluate the performance of the set of features using the trained model. Where the number of possible features is relatively small and/or training time is relatively short, all possible sets of features may be evaluated and the best performing set may be selected. Where the number of possible features is relatively large and/or the training time is a significant factor, optimization techniques may be used to iteratively find a set of features that performs well. In some implementations, a set of features may be selected using system 500, and then a subset of these features may be selected using wrapper methods as the final set of features.

Figure 7:
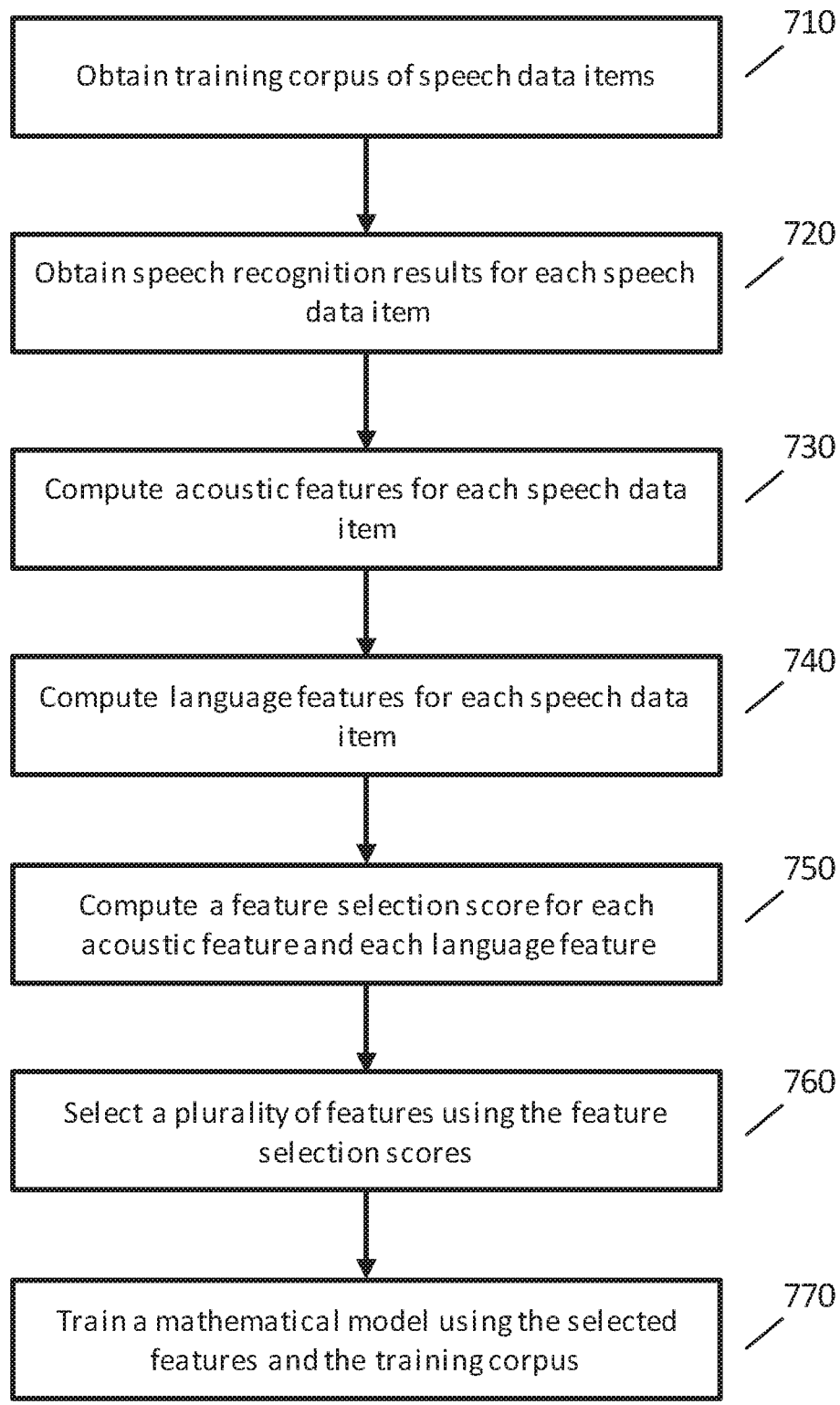
FIG. 7 is a schematic flowchart diagram illustrating one embodiment of a method for selecting features for training a mathematical model for diagnosing a medical condition.

FIG. 7 is a flowchart of an example implementation of selecting features for training a mathematical model for diagnosing a medical condition. In FIG. 7 and other flowcharts herein, the ordering of the steps is exemplary and other orders are possible, not all steps are required, steps may be combined (in whole or part) or sub-divided and, in some implementations, some steps may be omitted or other steps may be added. The methods described by any flowcharts described herein may be implemented, for example, by any of the computers or systems described herein.

At step 710, a training corpus of speech data items is obtained. The training corpus may include a representation of an audio signal of a person's speech, an indication of a medical diagnosis of the person from whom the speech was obtained, and any other appropriate information, such as any of the information described herein.

At step 720, speech recognition results are obtained for each speech data item of the training corpus. The speech recognition results may have been computed in advance and stored with the training corpus or stored in another location. The speech recognition results may include any appropriate information, such as a transcript, a list of highest scoring transcripts (e.g., an N-best list), a lattice of possible transcriptions, and timing information, such as the start and end time of words, pause fillers, or other speech units.

At step 730, acoustic features are computed for each speech data item of the training corpus. Acoustic features may include any features that are computed without using speech recognition results of a speech data item, such as any of the acoustic features described herein. Acoustic features may include or be computed from data used in the speech recognition process (e.g., mel-frequency cepstral coefficients or perceptual linear predictors), but acoustic features do not use speech recognition results, such as information about the words or pause fillers present in a speech data item.

At step 740, language features are computed for each speech data item of the training corpus. Language features may include any features that are computed using speech recognition results, such as any of the language features described herein.

At step 750, a feature selection score is computed for each acoustic feature and each language feature. To compute a feature selection score for the feature, the value of the feature for each speech data item in the training corpus may be used along with other information, such as a known diagnosis value corresponding to the speech data item. The feature selection score may be computed using any of the techniques described herein, such as by computing an absolute Pearson correlation. In some implementations, feature selection scores may be computed for other features as well, such as features relating to demographic information of a person.

At step 760, a plurality of features is selected using the feature selection scores. For example, a number of features having the highest selection scores may be selected. In some implementations, a stability determination may be computed for each feature and the plurality of features may be selected using both the feature selection scores and the stability determinations, such as by using any of the techniques described herein.

At step 770, a mathematical model is trained using the selected features. Any appropriate mathematical model may be trained, such as a neural network or a support vector machine. After the mathematical model has been trained, it may be deployed in a production system, such as a voice module 104, a system 109 of FIG. 1B, or the like to perform diagnosis of medical conditions.

The steps of FIG. 7 may be performed in a variety of manners. For example, in some implementations, steps 730, and 740 may be performed in a loop that loops over each of the speech data items in the training corpus. For a first iteration, acoustic and language features may be computed for a first speech data item, for a second iteration, acoustic and language features may be computed for a second speech data item, and so forth.

When using a deployed model for diagnosing a medical condition, the person being diagnosed may be presented with a sequence of prompts or questions to obtain speech from the person. Any appropriate prompts may be used, such as any of the prompts of FIG. 4. After the features have been selected, as described above, prompts may be selected so that the selected prompts provide useful information about the selected features.

For example, suppose that a selected feature is pitch. While pitch has been determined to be a useful feature for diagnosing a medical condition, some prompts may be better than others in obtaining a useful pitch feature. Very short utterances (e.g., yes/no answers) may not provide sufficient data to accurately compute pitch and thus prompts that generate longer responses may be more useful in obtaining information about pitch.

For another example, suppose that a selected feature is word difficulty. While word difficulty has been determined to be a useful feature for diagnosing a medical condition, some prompts may be better than others in obtaining a useful word difficulty feature. Prompts that ask a user to read a presented passage will generally result in speech of the words in the passage, and thus the word difficulty feature would have the same value each time this prompt is presented, and thus this prompt would not be useful in obtaining information about word difficulty. By contrast, open ended questions, such as "Tell me about your day?", may result in greater variability of vocabulary in responses and thus may provide more useful information about word difficulty.

Selecting a set of prompts may also improve the performance of a system for diagnosing medical conditions and provide a better experience for the person being evaluated. By using the same set of prompts for each person being evaluated, the system for diagnosing medical conditions may provide more accurate results, since the data collected from multiple people may be more comparable than if different prompts were used with each person. Further, using a defined set of prompts, allows the evaluation of a person to be more predictable and of a desired duration that is appropriate for the evaluation of the medical condition. For example, for evaluating whether a person has Alzheimer's disease, it may be acceptable to use more prompts to collect a larger amount of data, but for evaluating whether a person has a concussion during a sporting event, it may be necessary to use a smaller number of prompts to obtain a result more quickly.

In some implementations, prompts may be selected by computing prompt selection scores. A training corpus may have multiple or even many speech data items for a single prompt. For example, the training corpus may include examples of the prompt used with different people or the same prompt may be used with the same person multiple times.

Figure 8:
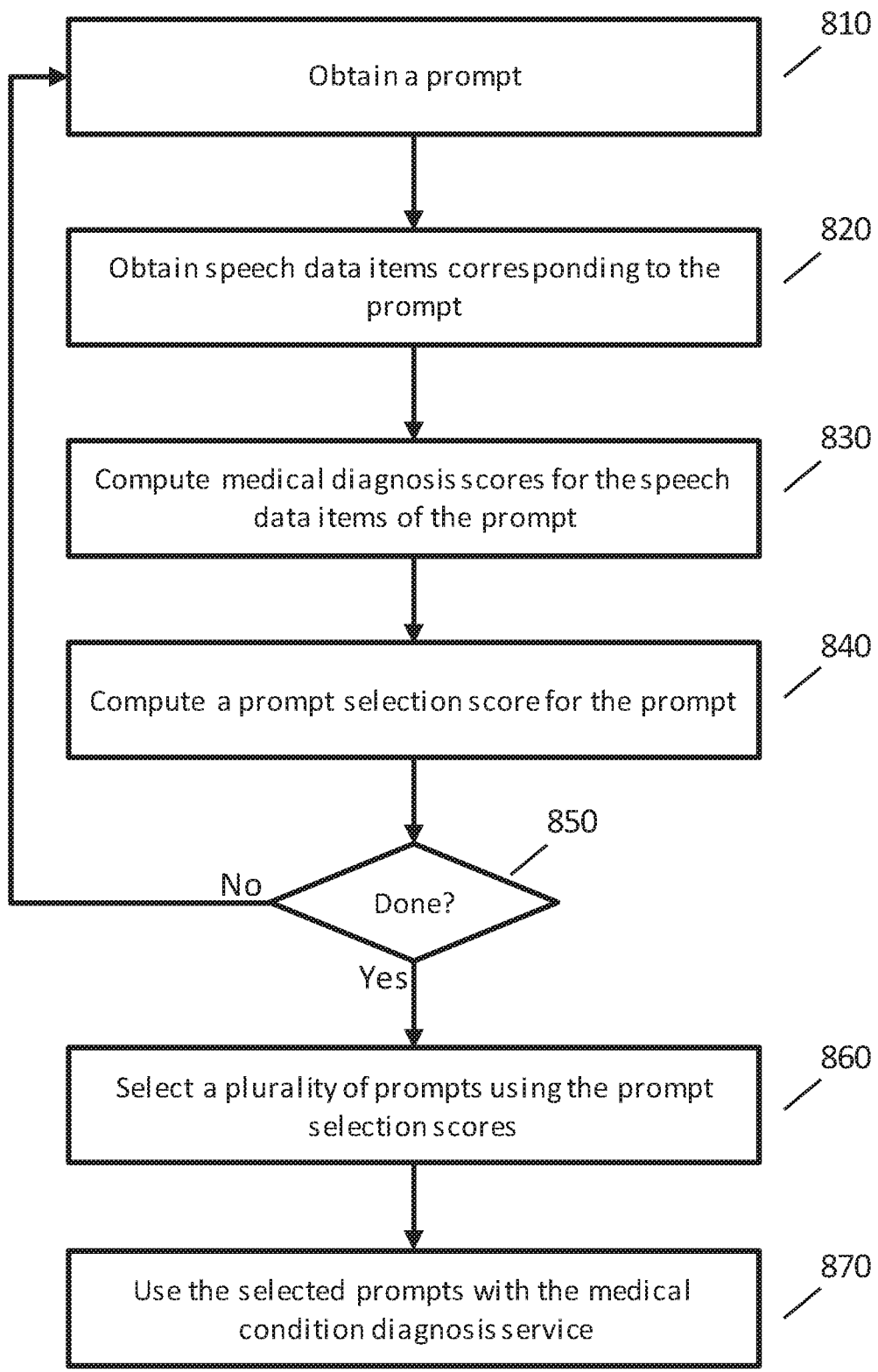
FIG. 8 is a schematic flowchart diagram illustrating one embodiment of a method for selecting prompts for use with a mathematical model for diagnosing a medical condition.

FIG. 8 is a flowchart of an example implementation of selecting prompts for use with a deployed model for diagnosing a medical condition.

Steps 810 to 840 may be performed for each prompt (or a subset of the prompts) in the training corpus to compute a prompt selection score for each prompt.

At step 810 a prompt is obtained, and at step 820 speech data items corresponding to the prompt are obtained from the training corpus.

At step 830, a medical diagnosis score is computed for each speech data item corresponding to the prompt. For example, a medical diagnosis score for a speech data item may be a number output by a mathematical model (e.g., the mathematical model trained in FIG. 7) indicating a likelihood that a person has the medical condition and/or a severity of the medical condition.

At step 840, a prompt selection score is computed for the prompt using the computed medical diagnosis scores. The computation of a prompt selection score may be similar to the computation of a feature selection score, as described above. For each speech data item corresponding to the prompt, a pair of numbers may be obtained. For each pair, the first number of the pair may be the computed medical diagnosis score computed from the speech data item, and the second number of the pair may be a known medical condition diagnosis of the person (e.g., the person is known to have the medical condition or a severity of the medical condition). Plotting these pairs of numbers may result in a plot similar to FIG. 6A or FIG. 6B, and depending on the prompt there may or may not be a pattern or correlation in the pairs of numbers.

A prompt selection score for a prompt may include any score that indicates a pattern or correlation between the computed medical diagnosis scores and the known medical condition diagnoses. For example, a prompt selection score may include a Rand index, an adjusted Rand index, mutual information, adjusted mutual information, a Pearson correlation, an absolute Pearson correlation, a Spearman correlation, or an absolute Spearman correlation.

At step 850 it is determined if other prompts remain to be processed. If prompts remain to be processed, then processing may proceed to step 810 to process additional prompts. If all prompts have been processed, then processing may proceed to step 860.

At step 860, a plurality of prompts are selected using the prompt selection scores. For example, a number of prompts having the highest prompt selection scores may be selected. In some implementations, a stability determination may be computed for each prompt and the plurality of prompts may be selected using both the prompt selection scores and the prompt stability determinations, such as by using any of the techniques described herein.

At step 870, the selected prompts are used with a deployed medical condition diagnosis service. For example, when diagnosing a person, the selected prompts may be presented to a person to obtain speech of the person in response to each of the prompts.

In some implementations, other techniques, such as wrapper methods, may be used for prompt selection or may be used in combination with the prompt selection techniques presented above. In some implementations, a set of prompts may be selected using the process of FIG. 8, and then a subset of these prompts may be selected using wrapper methods as the final set of features.

In some implementations, a person involved with creating the medical condition diagnosis service may assist in the selection of prompts. The person may use his knowledge or experience to select prompts based on the selected features. For example, where a selected feature is word difficulty, the person may review the prompts and select prompts that are more likely to provide useful information relating to word difficulty. The person may select one or more prompts that are likely to provide useful information for each of the selected features.

In some implementations, the person may review the prompts selected by the process of FIG. 8, and add or remove prompts to improve the performance of a medical condition diagnosis system. For example, two prompts may each provide useful information about word difficulty, but the information provided by the two prompts may be largely redundant, and using both prompts may not provide significant benefit over using just one of them.

In some implementations, a second mathematical model may be trained after prompt selection that is adapted to the selected prompts. The mathematical model trained in FIG. 7 may process a single utterance (in response to a prompt) to generate a medical diagnosis score. Where the process of performing a diagnosis comprises processing multiple utterances corresponding to multiple prompts, then each of the utterances may be processed by the mathematical model of FIG. 7 to generate multiple medical diagnosis scores. To determine an overall medical diagnosis, the multiple medical diagnosis scores may need to be combined in some way. Accordingly, the mathematical model trained in FIG. 7 may not be adapted to a selected set of prompts.

When the selected prompts are used in a session to diagnose a person, each of the prompts may be presented to the person to obtain an utterance corresponding to each of the prompts. Instead of processing the utterances separately, the utterances may be processed simultaneously by the model to generate a medical diagnosis score. Accordingly, a model may be adapted to the selected prompts because it is trained to simultaneously process utterances corresponding to each of the selected prompts.

Figure 9:
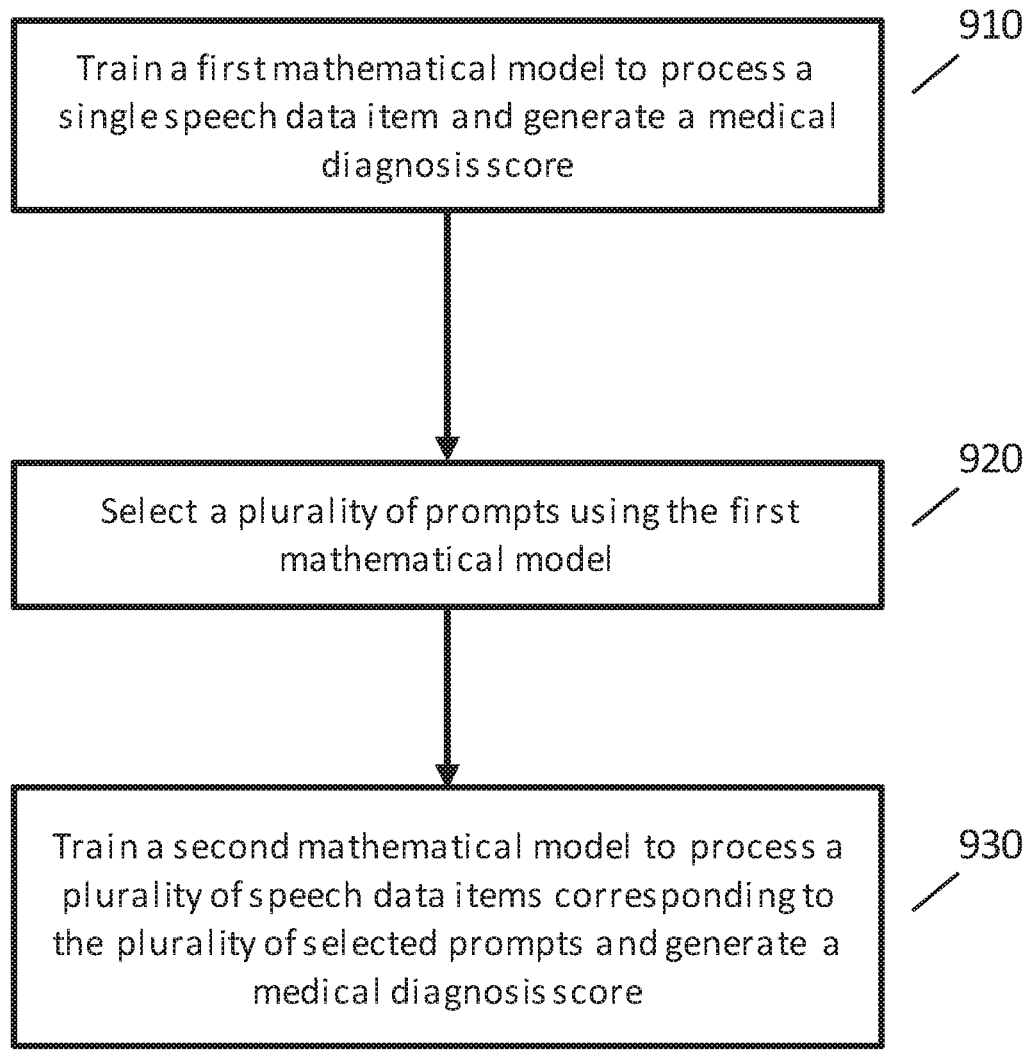
FIG. 9 is a schematic flowchart diagram illustrating one embodiment of a method for training a mathematical model for diagnosing a medical condition that is adapted to a set of selected prompts.

FIG. 9 is a flowchart of an example implementation training a mathematical model that is adapted to a set of selected prompts. At step 910, a first mathematical model is obtained, such as by using the process of FIG. 7. At step 920, a plurality of prompts are selected using the first mathematical model, such as by the process of FIG. 8.

At step 930, a second mathematical model is trained that simultaneously processes multiple speech data items corresponding to the plurality of selected prompts to generate a medical diagnosis score. When training the second mathematical model, a training corpus may be used that includes sessions with speech data items corresponding to each of the plurality of selected prompts. When training the mathematical model, the input to the mathematical model may be fixed to the speech data items from the session and corresponding to each of the selected prompts. The output of the mathematical model may be fixed to a known medical diagnosis. The parameters of the model may then be trained to optimally process the speech data item simultaneously to generate a medical diagnosis score. Any appropriate training techniques may be used, such as stochastic gradient descent.

The second mathematical model may then be deployed as part of a medical condition diagnosis service, such as a voice module 104, the service of FIG. 1, or the like. The second mathematical model may provide better performance than the first mathematical model because it has been trained to process the utterances simultaneously rather than individual and thus the training may be better able to combine the information from all the of utterances to generate the medical condition diagnosis score.

Figure 10:
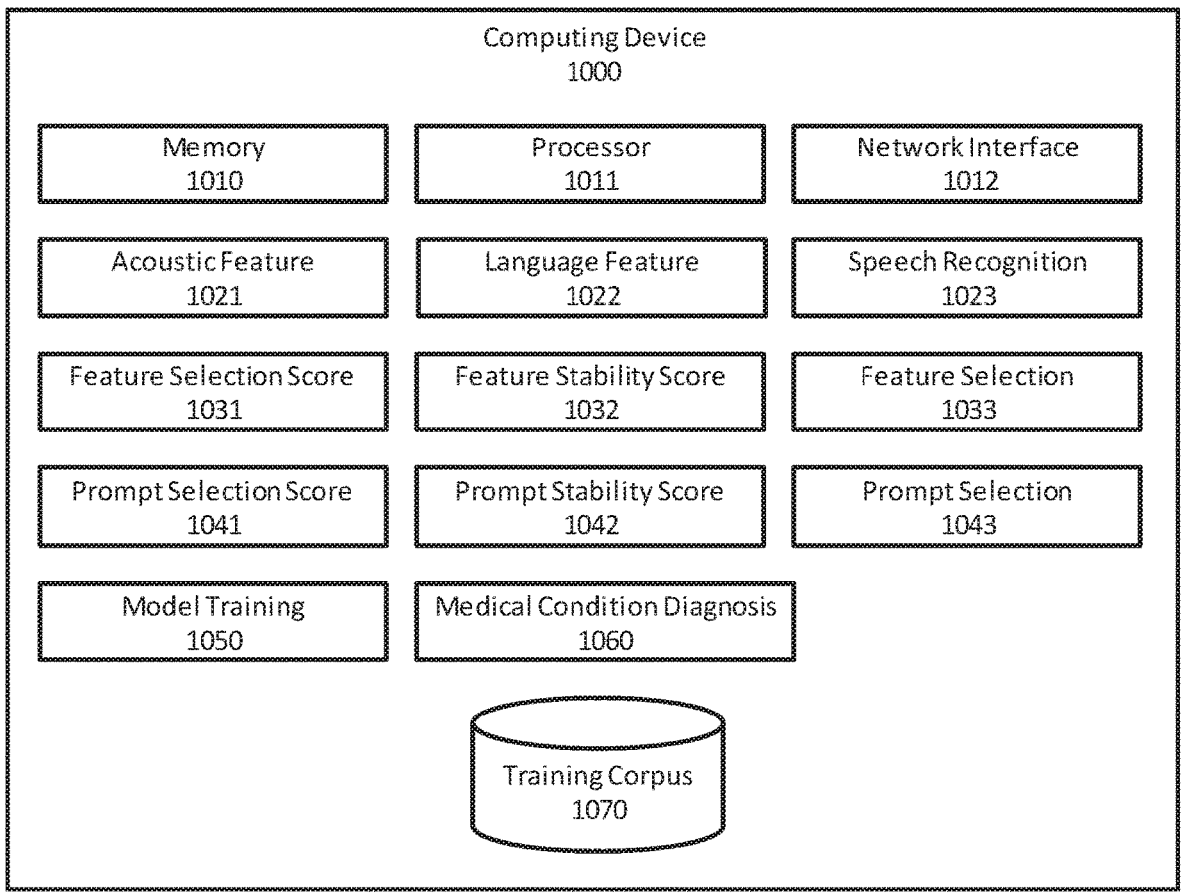
FIG. 10 is a schematic block diagram illustrating one embodiment of a computing device that may be used to train and deploy a mathematical model for diagnosing a medical condition.

FIG. 10 illustrates components of one implementation of a computing device 1000 for implementing any of the techniques described above. In FIG. 10, the components are shown as being on a single computing device, but the components may be distributed among multiple computing devices, such as a system of computing devices, including, for example, an end-user computing device (e.g., a smart phone or a tablet) and/or a server computing device (e.g., cloud computing).

Computing device 1000 may include any components typical of a computing device, such as volatile or nonvolatile memory 1010, one or more processors 1011, and one or more network interfaces 1012. Computing device 1000 may also include any input and output components, such as displays, keyboards, and touch screens. Computing device 1000 may also include a variety of components or modules providing specific functionality, and these components or modules may be implemented in software, hardware, or a combination thereof. Below, several examples of components are described for one example implementation, and other implementations may include additional components or exclude some of the components described below.

Computing device 1000 may have an acoustic feature computation component 1021 that may compute acoustic features for a speech data item as described above. Computing device 1000 may have a language feature computation component 1022 that may compute language features for a speech data item as described above. Computing device 1000 may have a speech recognition component 1023 that may generate speech recognition results for a speech data item as described above. Computing device 1000 may have a feature selection score computation component 1031 that may compute selection scores for features as described above. Computing device 1000 may have a feature stability score computation component 1032 that may make stability determinations or compute stability scores as described above. Computing device 1000 may have a feature selection component 1033 that may select features using selection scores and/or stability determinations as described above. Computing device 1000 may have a prompt selection score computation component 1041 that may compute selection scores for prompts as described above. Computing device 1000 may have a prompt stability score computation component 1042 that may make stability determinations or compute stability scores as described above. Computing device 1000 may have a prompt selection component 1043 that may select prompts using selection scores and/or stability determinations as described above. Computing device 1000 may have a model training component 1050 that may train mathematical models as described above. Computing device 1000 may have a medical condition diagnosis component 1060 that may process speech data items to determine a medical diagnosis score as described above.

Computing device 1000 may include or have access to various data stores, such as training corpus data store 1070. Data stores may use any known storage technology such as files, relational or non-relational databases, or any non-transitory computer-readable media.

Figure 11:
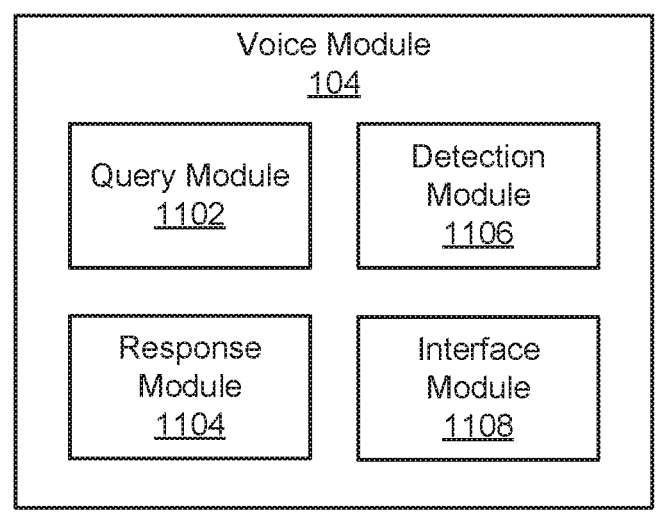
FIG. 11 is a schematic block diagram illustrating one embodiment of a voice module.

FIG. 11 depicts one embodiment of a voice module 104. The voice module 104, in certain embodiments, may be substantially similar to one or more of a device voice module 104a and/or a backend voice module 104b, as described above with regard to FIG. 1A. The voice module 104, in the depicted embodiment, includes a query module 1102, a response module 1104, a detection module 1106, and an interface module 1108.

In one embodiment, the query module 1102 questions and/or queries a user with one or more questions, prompts, requests, or the like. The query module 1102, in certain embodiments, may audibly and/or verbally question a user (e.g., using a speaker of a computing device 102 such as an integrated speaker, headphones, a Bluetooth® speaker or headphones, or the like). For example, due to certain potential medical conditions, such as a concussion, it may be difficult for a user to read a question and/or prompt, and audibly questioning the user may simplify and/or expedite a diagnosis. In a further embodiment, the query module 1102 may display one or more questions and/or other prompts to a user (e.g., on an electronic display screen of a computing device 102, or the like), another user (e.g., a coach, a parent, a medical professional, an administrator, or the like) may read one or more questions and/or other prompts to a user, or the like. In various embodiments, the one or more questions or prompts may be selected as described above with regard to the prompt selection component 1043, or the like, in order to facilitate a diagnosis of one or more medical conditions.

In certain embodiments, a plurality of query modules 1102 disposed on a plurality of different computing devices 102 may query and/or question a plurality of different users. For example, a plurality of distributed query modules 1102 may collect voice samples for a medical trial, to train a machine learning model for diagnosing a medical condition, to collect test data to facilitate prompt selection, or the like.

The query module 1102, in one embodiment, questions and/or otherwise queries a user at a predefined health state, such as a known healthy state, a predefined stage of a medical condition, or the like, to collect one or more baseline voice recordings, training data, or other data. In certain embodiments, the query module 1102 questions and/or otherwise queries a user in response to a potential medical event or other trigger. The query module 1102 may question a user in order to collect test case voice recordings or other test case data in response to a user requesting a medical assessment, based on data from a sensor of a computing device 102 such as a wearable or mobile device, and/or based on receiving another trigger indicating that an injury may have occurred, that one or more symptoms of a disease have been detected, or the like. For example, in response to a hit, a fall, an accident, and/or another potential concussion event (e.g., at a sporting event or other activity), a user (e.g., an injured player or other person, a coach, a parent, a medical professional, an administrator, or the like) may request a medical assessment (e.g., using a graphical user interface of the interface module 1108 to trigger one or more questions from the query module 1102, collection of voice data and/or other data from the response module 1104, and/or a medical assessment from the detection module 1106, or the like). A concussion, in certain embodiments, may comprise a disturbance in brain function causes by a direct or indirect force to the head of a user. A concussion may cause a headache, unsteadiness, confusion or other impaired brain function, abnormal behavior and/or personality, or the like.

For example, in embodiments where the medical condition comprises a concussion, the query module 1102 may audibly question a user and/or collect sensor data associated with the user to detect whether the user's eyes are opening, whether the user's eyes are opening in response to pain, whether the user's eyes are opening in response to speech, whether the user's eyes are opening spontaneously, whether the user can provide a verbal response, whether the user is making incomprehensible sounds, whether the user is responding to questions or other prompts with inappropriate words, whether the user is confused, whether the user is disoriented, whether the user provides little or no motor response, whether the user exhibits extension to pain (e.g., arm abduction, supination of forearm, or the like), whether the user exhibits abnormal flexion to pain (e.g., pronation of forearm, flexor posturing, or the like), whether the user withdraws from pain, whether the user localizes pain (e.g., purposeful movement toward pain), whether the user obeys verbal/audible commands from the query module 1102, or the like. The query module 1102, in some embodiments, may direct some questions to a user being assessed and/or diagnosed, and others to an administrator (e.g., a medical professional, a coach, a parent, a trainer, or the like). For example, the query module 1102 may question an administrator about one or more signs the administrator may have observed in the user being assessed and/or diagnosed, such as a lack of balance, motor incoordination, disorientation, confusion, loss of memory, a blank or vacant look, a visible facial injury or other injury, observed results of a physical examination (e.g., range of motion, tenderness, sensation, strength, a balance examination, a coordination examination, or the like), and/or another observation.

In certain embodiments, the query module 1102 may question and/or prompt a user about the sporting event in which the user was participating when the potential medical event occurred, the user's team, the date and/or time, memory test questions, or the like. For example, the query module 1102 may audibly and/or textually question the user "what venue are we at today?", "which half is it now?", "who scored last in this match?", "what team did you play last week/game?", "did your team win the last game?", "what month is it?", "what is the date today?", "what is the day of the week?", "what year is it?", "what time is it right now?", may audibly list words and/or numbers for the user and ask the user to repeat them back, may display a series of pictures to the user and ask the user to repeat back a description of the series of pictures, or the like. One or more questions and/or prompts of the query module 1102 may allow the detection module 1106 to determine a Standardized Concussion Assessment Tool (SCAT) score, a SCAT2 score, a SCAT3 score, a SCAT5 score, a Glasgow Coma Score (GCS), a Maddocks Score, a Concussion Recognition Tool (CRT) score, and/or another concussion score.

In one embodiment, the response module 1104 is configured to receive response data (e.g., voice data of a verbal response, text data of a typed response, sensor data, image and/or video data from a camera or other image sensor, touch input from a touchscreen and/or touchpad, movement information from an accelerometer and/or gyroscope, or the like), in response to one or more questions and/or other queries from the query module 1102. For example, in certain embodiments, the response module 1104 may use a microphone of a computing device 102 (e.g., a mobile computing device 102 which may be transported to a football field, another sporting event, or the like) to record verbal responses (e.g., answers) of a user to one or more questions or other prompts from the query module 1102.

The response module 1104, in one embodiment, may store received response data such as voice recordings, sensor data, or the like on a computer readable storage medium of a computing device 102, 110, so that the detection module 1106 may access and/or process the received response data to diagnose and/or assess a medical condition, train a model for diagnosing and/or assessing a medical condition, or the like; so that the interface module 1108 may provide the received response data to one or more authorized users; and/or so that the received response data is otherwise accessible for use. In another embodiment, the response module 1104 may provide received response data directly to the detection module 1106 for diagnosing and/or assessing a medical condition (e.g., without otherwise storing the data, temporarily storing and/or caching the data, or the like).

The response module 1104 may separately receive and/or store baseline response data (e.g., in response to one or more baseline questions or prompts from the query module 1102) and test case response data (e.g., in response to one or more test case questions or prompts from the query module based on a potential medical event, or the like). In certain embodiments, the response module 1104 may only receive test case response data, and the detection module 1106 may base an assessment or other diagnosis of a medical condition on the test case data and an analysis of data from different users (e.g., different users known to have the medical condition, or the like). The response module 1104 may store and/or organize received response data in a database and/or other predefined data structure accessible by the detection module 1106, the interface module 1108, or the like.

By storing a history of a user's responses (e.g., baseline response data, test case response data, assessments, scores, or the like), in certain embodiments, the response module 1104 may enable the detection module 1106 to dynamically assess a medical condition for the user in response to a medical event. For example, the response module 1104 may store response data for a user on a mobile computing device 102, on a backend server 108 in communication with a mobile computing device 102 over a data network 106, 130, or the like, enabling the detection module 1106 to determine an assessment of a medical condition on location in response to a potential medical event (e.g., on the sideline or field at a football game or other sporting event in response to a potential concussion event, in response to a motor vehicle accident, or the like).

In one embodiment, the detection module 1106 is configured to provide an assessment and/or other diagnosis for a user of a medical condition based on an analysis of one or more received responses of a user from the response module 1104. The detection module 1106, in various embodiments, may comprise, be in communication with, and/or be substantially similar to the acoustic feature computation component 210, the speech recognition component 220, the language feature computation component 230, and/or the medical condition classifier 240 described above.

In one embodiment, the detection module 1106 may determine an assessment or other diagnosis of a medical condition for a user (e.g., indicating whether or not the user has the medical condition, a likelihood that the user has the medical condition, an estimated severity of the medical condition, or the like) based on both test case response data for the user and previously received baseline response data for the same user (e.g., in order to determine changes in the user's voice, changes in the user's responses, or the like). In other embodiments, the detection module 1106 may determine an assessment or other diagnosis of a medical condition for a user based on test case response data for the user and based on response data for different users (e.g., different users previously diagnosed with the medical condition, or the like). In a further embodiment, the detection module 1106 may determine an assessment or other diagnosis of a medical condition for a user based on test case response data for the user, baseline response data for the same user, and response data for different users, or the like.

As described above with regard to the acoustic feature computation component 210, the speech recognition component 220, the language feature computation component 230, and/or the medical condition classifier 240, in certain embodiments, the detection module 1106 may extract one or more voice features (e.g., acoustic features and/or language features) from a voice recording (e.g., baseline response data and/or test case response data) and may input the one or more extracted voice features into a model associated with a medical condition (e.g., a machine learning model such as a Gaussian mixture model, an acoustic model, a language model, a neural network, a deep neural network, a classifier, a support vector machine, a multi-layer perceptron, or the like), which may output an assessment or other diagnosis for the medical condition based on the one or more extracted voice features.

In a further embodiment, in addition to inputting extracted voice features into a model to diagnose a medical condition, the detection module 1106 may input other supplemental data associated with the user into the model, and may diagnose the medical condition based on the result. For example, the detection module 1106 may input sensor data from a computing device 102 of a user into a model (e.g., together with extracted voice features or other voice data) to determine an assessment or other diagnoses of a medical condition for a user.

In one embodiment, the detection module 1106 may extract one or more image features from image data (e.g., one or more images, video, or the like of the user, of the user's face, of another body part of the user associated with a medical condition, or the like) from an image sensor such as a camera of a computing device 102, and may input the one or more image features into a model (e.g., with extracted voice features or the like). In a further embodiment, the detection module 1106 may base an assessment or other diagnosis at least partially on touch inputs received from a user on a touchscreen, touchpad, or the like of a computing device 102.

For example, the query module 1102 may provide an interactive video game or the like on an electronic display of a computing device 102, and the interactive video game may be configured to test a user for one or more symptoms of a medical condition (e.g., testing reflexes, dexterity, reaction time, or the like) and the detection module 1106 may extract one or more features from touch inputs received from the user during the interactive video game (e.g., a score in the video game, reaction times of the user, touch accuracy metrics for the user, or the like) and may input the one or more extracted features into a model for diagnosing a medical condition (e.g., with one or more extracted voice features, or the like). In certain embodiments, the detection module 1106 may extract one or more features from movement information measured by an accelerometer, a gyroscope, and/or another movement sensor of a mobile computing device 102 for a user, and may input the one or more extracted features into a model for diagnosing a medical condition (e.g., with one or more extracted voice features, or the like).

As described above, in certain embodiments, the detection module 1106 may determine an assessment or other diagnosis for a medical condition comprising a neurological condition such as a concussion. In other embodiments, the detection module 1106 may determine an assessment or other diagnosis for a medical condition comprising one or more of depression, stress, stroke, cognitive well-being, mood, honesty, Alzheimer's disease, Parkinson's disease, cancer, or the like.

In certain embodiments, the detection module 1106 may be configured to determine an assessment or other diagnosis of a medical condition based on one or more acoustic features of received verbal response data, without regard to one or more language features of the received verbal response data (e.g., without any language features, with only one or more predefined language features, without any automatic speech recognition, or the like). In this manner, in some embodiments, the assessment and/or diagnosis of the detection module may be independent of a language and/or a dialect of the received verbal response, so the detection module 1106 may provide assessments and/or diagnoses for users in different languages using acoustic features of the received verbal response data. In other embodiments, the detection module 1106 may base an assessment and/or diagnosis of a medical condition on both acoustic features and language features of received verbal response data.

In certain embodiments, the detection module 1106 may determine an assessment and/or diagnosis of a medical condition exclusively on a mobile computing device 102 of a user. For example, in an emergency situation, or the like, a diagnosis may be needed as soon as possible, and there may not be time to upload recorded verbal responses to a backend server 108 for processing, or a mobile computing device 102 may not have a connection to a data network 106, 130, or may not have a fast enough connection. The detection module 1106, in one embodiment, may use one or more models configured to execute using processing power, volatile memory capacity, and/or non-volatile storage capacity available on a mobile computing device 102. For example, a model used by a detection module 1106 on a mobile computing device may minimize the size of classifiers (e.g., the required volatile and/or non-volatile storage capacity) by limiting matrix multiplication in the model (e.g., no matrix multiplication, only a predefined number of matrix multiplications, or the like), even if using additional matrix multiplication may improve the accuracy of the assessment and/or diagnosis.

In one embodiment, the detection module 1106 determines the sole and/or exclusive assessment and/or diagnosis on a mobile computing device 102. In a further embodiment, a detection module 1106 may determine a first assessment and/or diagnosis (e.g., a first score) on a mobile computing device 102, and another detection module 1106 may determine a second assessment and/or diagnosis (e.g., a second score, a more accurate and/or more detailed assessment, or the like). In another embodiment, the detection module 1106 may determine the sole and/or exclusive assessment and/or diagnosis on a backend server device 108.

In certain embodiments, a plurality of voice modules 104 may be configured to perform one or more medical trials with users comprising medical trial participants (e.g., determining the efficacy of a medical treatment based on an analysis of voice data from participants). In such embodiments, the detection module 1106 may determine an assessment of an efficacy of a medical treatment for the medical condition associated with the medical trial. For example, users, as medical trial participants, may be divided into at least a placebo group that doesn't receive the medical treatment and a different group that receives the medical treatment, or into multiple groups that receive different medical treatments, or the like.

A plurality of distributed detection modules 1106 may be configured to provide blind assessments of a medical condition for both a placebo group and one or more groups receiving a medical treatment, allowing one or more administrators of the medical trial to determine an efficacy of the medical treatment. For example, the detection module 1106 may determine a severity of a medical condition, a severity of one or more symptoms of a medical condition, or the like for the placebo group and for the group receiving the medical treatment and compare the two. A "blind" assessment, as used herein, is an assessment that is not based on whether or not a participant is in a placebo group or in a group receiving a medical treatment. For example, in certain embodiments, a detection module 1106 may use the same model, the same analysis, or the like for both medical trial participants in a placebo group and medical trial participants in a group receiving a medical treatment.

In certain embodiments, instead of basing an assessment solely on the efficacy of a medical treatment at treating the medical condition associated with the medical trial, the detection module 1106 is configured to base an assessment at least partially on one or more biomarkers of received response data (e.g., verbal response data, sensor data, or the like) indicating a quality of life for the user. For example, in addition to assessing the medical condition associated with a medical trial, the detection module 1106 may assess one or more quality of life biomarkers indicating physical fatigue, tiredness, mental fatigue, stress, anxiety, depression, and/or other parameters associated with a quality of life of the user. A biomarker, as used herein, comprises a measurable indicator from a user of some biological state and/or condition of the user (e.g., presence of a disease and/or injury, presence of one or more symptoms, a current quality of life of a user, or the like). A biomarker, in certain embodiments, may comprise a characteristic objectively identifiable by the detection module 1106 in response data from a user, such as an acoustic feature, a language feature, a characteristic identifiable in sensor data, or the like.

The detection module 1106, in certain embodiments, may initially use baseline response data from users (e.g., prospective medical trial participants) to screen participants for a medical trial (e.g., determine an assessment comprising a suitability of a user for the medical trial for a medical condition, or the like). For example, a cancer drug therapy may be effective, however, it may be detrimental to the quality of life of the individual using the cancer drug therapy. Instead of subjectively measuring the quality of life and/or behavioral consequences of receiving treatment or drugs using a questionnaire or similar tool, in certain embodiments, the detection module 1106 may identify one or more quality of life changes in a user (e.g., a medical trial participant) objectively using biomarkers or other indicators in verbal response data from the user.

The interface module 1108, in certain embodiments, cooperates with the query module 1102 to display one or more questions and/or prompts to a user (e.g., instead of audibly questioning the user, in addition to audibly questioning the user, or the like). The response module 1104 may display one or more user interface elements (e.g., a play button, a replay button, a next question button, a previous question button, or the like) allowing a user to navigate through one or more questions of the query module 1102. In one embodiment, the determination module 1106 may determine whether an answer from a user to a question from the query module 1102 is correct or incorrect (e.g., based on a voice analysis using a machine learning model, or the like) and the interface module 1108 may graphically mark the answer correct or incorrect (e.g., dynamically, during the query module 1102's administration of an assessment, or the like). In a further embodiment, the determination module 1106 may use automatic speech recognition to translate recorded voice responses of a user from the response module 1104 to text, which the interface module 1108 may display to the user (e.g., dynamically, in real time, or the like).

In certain embodiments, the interface module 1108 (e.g., in cooperation with the query module 1102), may prompt a user to recite a passage (e.g., a passage including sentences, sets of words, letters, numbers, monosyllables, or the like). The interface module 1108 may prompt the user to recite the same passage and/or set of passages each time data is collected (e.g., baseline response data collection, test case response data collection, medical trial screening data collection, medical trial data collection, or the like).

The interface module 1108, in some embodiments, may prompt an administrator of an assessment (e.g., a coach, a parent, a medical professional, or the like) with instructions to perform one or more physical examinations of a user being assessed. For example, the interface module 1108 may provide instructions for a balance examination, a motor coordination examination, a range of motion examination, a tenderness examination, a touch sensation examination, a strength examination, or the like, and may provide an interface for the administrator to record the results (e.g., the administrator's observations) for the response module 1104.

In one embodiment, the interface module 1108 provides one or more users with access to received response data from the response module 1104 (e.g., voice recordings, baseline response data, test case response data, sensor data, or the like), to assessments and/or other diagnoses from the detection module 1106, or the like. The interface module 1108 may allow a user to access received response data, assessments and/or other diagnoses, or the like from multiple locations (e.g., from a mobile app on a mobile computing device 102, from a web browser of a different computing device 102 accessing a web server of a backend server 108, or the like).

For example, the interface module 1108 may provide a user with a baseline assessment and/or score based on baseline response data, a test case assessment and/or score based on test case response data, a follow-up assessment and/or score based on subsequent responses (e.g., an at home follow-up assessment during recovery from a previously assessed/diagnosed medical condition), or the like, each through the same graphical user interface on one or more computing devices 102, along with the associated response data for each assessment and/or score, or the like. The interface module 1108 may display a baseline assessment and/or score next to a current (e.g., test case) assessment and/or score for comparison (e.g., side by side), may display a difference between a baseline assessment and/or score and a current (e.g., text case) assessment and/or score, or the like. In one embodiment, the interface module 1108 may display a breakdown of an assessment and/or score, with sub-scores in different categories, or the like.

The interface module 1108, in some embodiments, may aggregate response data, scores or other assessments, or the like for a user from multiple sports, teams, schools, or the like, and display them in a single graphical user interface. In this manner, the interface module 1108 may provide medical professionals, coaches, administrators, or the like, a more complete history and/or status of the user's health, injury history, or the like, for more informed medical decisions.

In certain embodiments, the interface module 1108 may enforce access control permissions (e.g., for privacy, for security, for HIPAA compliance, or the like) by authenticating users (e.g., with a username and password or other authentication credentials) and providing the users access to voice recordings or other response data, assessments or other diagnoses, or the like based on access control permissions associated with the user. In certain embodiments, the interface module 1108 enforces hierarchical access control permissions for different users, with users at each level in the hierarchy having access to data associated with any levels below their level in the hierarchy.

For example, in an embodiment where the voice module 104 is configured to diagnose concussions and/or another medical condition for athletes, athletes, parents, and/or guardians may have access permissions for the athletes' own personal response data (e.g., voice recordings), assessments and/or other diagnoses; a coach may have access to similar data for each team member (e.g., multiple athletes or other users); a school or league administrator may have access to similar data for team members of multiple teams (e.g., each team at the school, each team in the league, or the like); a district or region administrator may have access to similar data for team members of multiple schools or leagues; or the like. In certain embodiments, the interface module 1108 may anonymize data (e.g., response data such as voice recordings and/or sensor data, assessments and/or other diagnoses, or the like) for certain users, such as providing personalized information for an individual and their coach, but averaged or otherwise anonymized data (e.g., by team, by school, by position, by league, or the like) for other levels in a hierarchy.

In an embodiment where the voice module 104 is conducting a medical study, the interface module 1108 may block individual users (e.g., medical study participants) from accessing at least a portion of their own data (e.g., response data, assessments or other diagnoses, both response data and assessments, or the like), while the interface module 1108 may provide one or more administrators of the medical trial with hierarchical access control permissions with access the stored data for the users (e.g., stored baseline recorded verbal responses, test case recorded verbal responses, assessments or other diagnoses, or the like).

Figure 12:
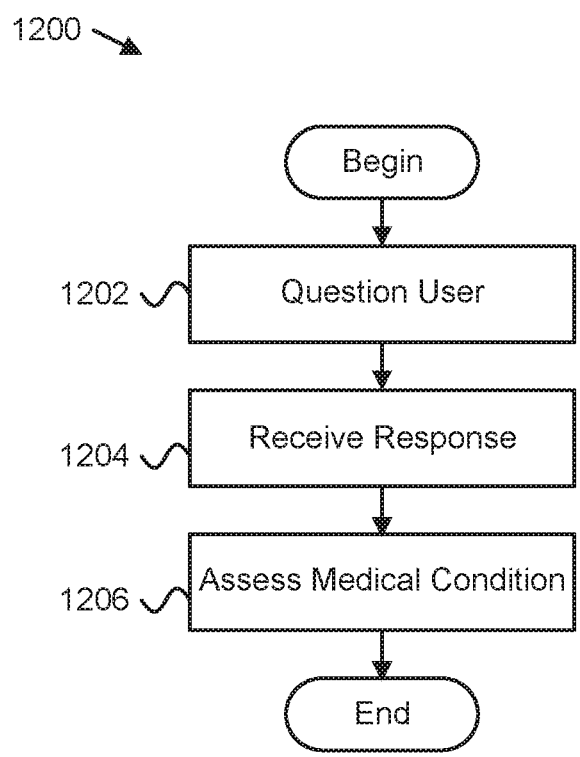
FIG. 12 is a schematic flowchart diagram illustrating one embodiment of a method for medical assessment based on voice.

FIG. 12 depicts one embodiment of a method 1200 for medical assessment based on voice. The method 1200 begins, and a query module 1102 questions 1202 a user (e.g., audibly from a speaker of a computing device 102, textually on an electronic screen of a computing device 102, or the like).

A response module 1104 receives 1204 a response of the user (e.g., a verbal response from a microphone of a computing device 102, a touch response from a touchscreen and/or touchpad of a computing device 102, sensor input from one or more sensors of a computing device 102, a selection or click from a mouse or other input device of a computing device 102, a text response input by the user on a keyboard and/or touchscreen of a computing device 102, or the like). A detection module 1106 assesses 1206 the user for a medical condition based on an analysis of the received 1204 response of the user and the method 1200 ends.

Figure 13:
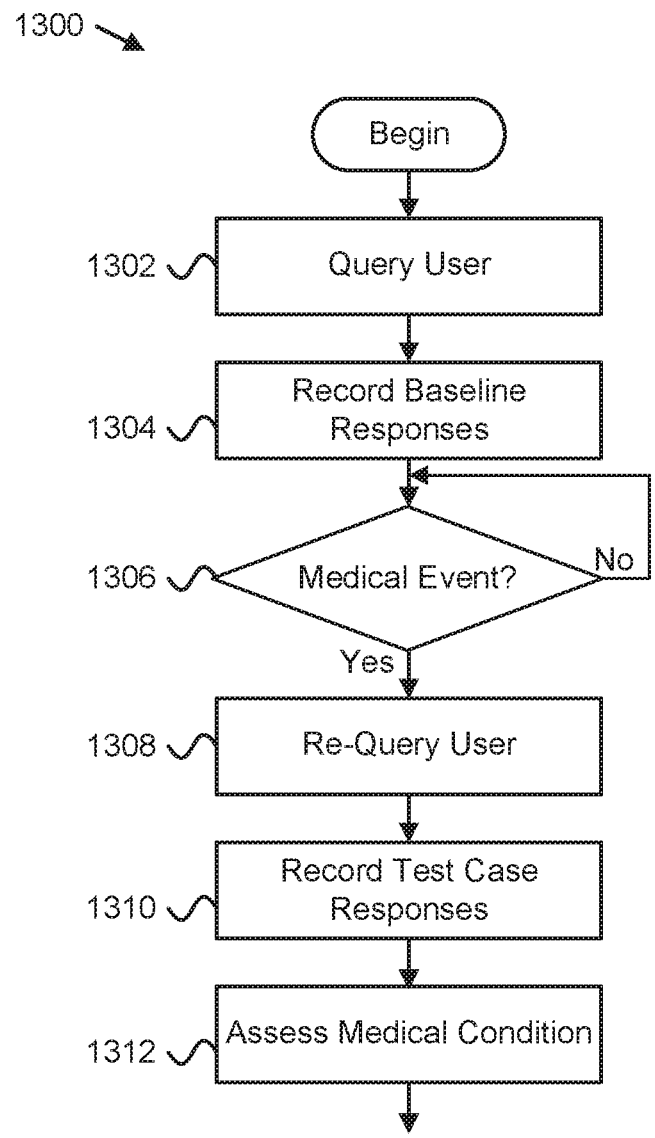
FIG. 13 is a schematic flowchart diagram illustrating a further embodiment of a method for medical assessment based on voice.

FIG. 13 depicts one embodiment of a method 1300 for medical assessment based on voice. A query module 1102 queries 1302 a user with one or more questions using a user interface of a computing device 102 (e.g., a microphone, an electronic display screen, a touchscreen, and/or one or more other sensors). A response module 1104 records 1304 one or more baseline responses (e.g., verbal responses as audio recordings, text responses and/or sensor data as a data file or other data structure, or the like) of the user to the queried 1302 one or more questions on a computing device 102, 108.

A detection module 1106 detects 1306 a potential medical event (e.g., based on a user requesting a medical assessment, based on data from a sensor, and/or based on receiving another trigger). If the detection module 1106 does not detect 1306 a potential medical event, the method 1300 continues until the detection module 1106 detects 1306 a potential medical event.

In response to the detection module 1106 detecting 1306 a potential medical event (e.g., an impact or other event that may have caused a concussion; an indicator of a potential medical condition such as depression, stress, stroke, cognitive well-being, mood, honesty, Alzheimer's disease, Parkinson's disease, or the like; a request from a user; and/or another trigger), the query module 1102 re-queries 1308 the user with one or more questions using a user interface of a computing device 102.

A response module 1104 records 1310, on a computing device 102, 108, one or more test case responses of the user to the re-queried 1308 one or more questions. A detection module 1106 assesses 1312, on a computing device 102, 108, a likelihood that the user has a medical condition (e.g., concussion, depression, stress, stroke, cognitive well-being, mood, honesty, Alzheimer's disease, Parkinson's disease, or the like) based on a voice analysis of the recorded 1304 one or more baseline responses and the recorded 1310 one or more test case responses. The method 1300 continues until the detection module 1106 detects 1306 a subsequent potential medical event.

A means for questioning a user (e.g., audibly and/or otherwise) from a computing device 102, in various embodiments, may comprise a voice module 104, a device voice module 104a, a backend voice module 104b, a query module 1102, a mobile computing device 102, a backend server computing device 108, an electronic speaker of a computing device 102, 108, headphones, an electronic display screen of a computing device 102, 108, a user interface device, a network interface, a mobile application, a processor, an application specific integrated circuit (ASIC), a field programmable gate array (FPGA), programmable logic, other logic hardware, and/or other executable program code stored on a non-transitory computer readable storage medium. Other embodiments may comprise substantially similar or equivalent means for questioning a user.

A means for receiving a response (e.g., a verbal response, a textual response, sensor data, or the like) of a user on a computing device 102, 108, in various embodiments, may comprise a voice module 104, a device voice module 104a, a backend voice module 104b, a response module 1104, a mobile computing device 102, a backend server computing device 108, a microphone, a user input device, a touch screen, a touchpad, a keyboard, a mouse, an accelerometer, a gyroscope, an image sensor, a mobile application, a processor, an application specific integrated circuit (ASIC), a field programmable gate array (FPGA), programmable logic, other logic hardware, and/or other executable program code stored on a non-transitory computer readable storage medium. Other embodiments may comprise substantially similar or equivalent means for receiving a response.

A means for assessing a user for a medical condition based on a received response of the user, in various embodiments, may comprise a voice module 104, a device voice module 104a, a backend voice module 104b, a detection module 1106, a mobile computing device 102, a backend server computing device 108, a mobile application, machine learning, artificial intelligence, an acoustic feature computation component 210, a speech recognition component 220, a Gaussian mixture model, an acoustic model, a language model, a neural network, a deep neural network, a medical condition classifier 240, a classifier, a support vector machine, a multi-layer perceptron, a processor, an application specific integrated circuit (ASIC), a field programmable gate array (FPGA), programmable logic, other logic hardware, and/or other executable program code stored on a non-transitory computer readable storage medium. Other embodiments may comprise substantially similar or equivalent means for assessing a user for a medical condition.

A means for authenticating different users in a hierarchy of users, in various embodiments, may comprise a voice module 104, a device voice module 104a, a backend voice module 104b, an interface module 1108, a mobile computing device 102, a backend server computing device 108, a mobile application, a processor, an application specific integrated circuit (ASIC), a field programmable gate array (FPGA), programmable logic, other logic hardware, and/or other executable program code stored on a non-transitory computer readable storage medium. Other embodiments may comprise substantially similar or equivalent means for authenticating different users.

A means for providing access to different recordings and/or different assessments to different users (e.g., based on hierarchical access control permissions for the hierarchy of users, or the like), in various embodiments, may comprise a voice module 104, a device voice module 104a, a backend voice module 104b, an interface module 1108, a mobile computing device 102, a backend server computing device 108, a mobile application, a processor, an application specific integrated circuit (ASIC), a field programmable gate array (FPGA), programmable logic, other logic hardware, and/or other executable program code stored on a non-transitory computer readable storage medium. Other embodiments may comprise substantially similar or equivalent means for providing access to different recordings and/or different assessments to different users.

The methods and systems described herein may be deployed in part or in whole through a machine that executes computer software, program codes, and/or instructions on a processor. "Processor" as used herein is meant to include at least one processor and unless context clearly indicates otherwise, the plural and the singular should be understood to be interchangeable. Any aspects of the present disclosure may be implemented as a method on the machine, as a system or apparatus as part of or in relation to the machine, or as a computer program product embodied in a computer readable medium executing on one or more of the machines. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
   a query module installed on a computing device and configured to question a user from one or more of an electronic display screen and a speaker of the computing device with one or more open ended questions comprising prompts selected from a larger plurality of prompts based on a prompt selection score for each prompt, the prompt selection scores computed using medical diagnoses scores for speech data items of a training corpus;
   a response module installed on the computing device and configured to receive a conversational verbal response of the user from a microphone of the computing device in response to the one or more open ended questions; and
   a detection module installed on the computing device and configured to provide a machine learning assessment for the user of a medical condition based on a machine learning analysis of the received conversational verbal response of the user.

2. The apparatus of claim 1, wherein the detection module is configured to determine the machine learning assessment based on one or more acoustic features of the received conversational verbal response without regard to language features of the received conversational verbal response such that the machine learning assessment is independent of one or more of a language and a dialect of the received conversational verbal response.

3. The apparatus of claim 1, wherein the one or more open ended questions result in variability of vocabulary in the received conversational verbal response.

4. The apparatus of claim 3, wherein the the detection module is configured to determine a word feature based on the vocabulary in the received conversational verbal response and the machine learning assessment for the user is based at least partially on the determined word feature.

5. The apparatus of claim 4, wherein the detection module is configured to determine the word feature using statistics of 1-gram probabilities of spoken words of the received conversational verbal response.

6. The apparatus of claim 4, wherein the detection module is configured to determine the word feature by classifying spoken words of the received conversational verbal response according to their frequency percentiles.

7. The apparatus of claim 1, wherein the one or more open ended questions are determined by:
   computing the medical diagnosis score for each of the speech data items of the training corpus by processing the speech data items with a mathematical model;
   computing the prompt selection score for each prompt of the plurality of prompts using the medical diagnosis scores; and
   selecting a subset of prompts from the plurality of prompts using the prompt selection scores, the selected subset of prompts comprising the one or more open ended questions.

8. The apparatus of claim 1, wherein the medical condition comprises a concussion.

9. The apparatus of claim 1, wherein the medical condition comprises one or more of depression, a stroke, Alzheimer's disease, and Parkinson's disease.

10. The apparatus of claim 1, further comprising an interface module configured to play a recording of the received conversational verbal response of the user and recordings of received conversational verbal responses of a plurality of other users to a different user based on hierarchical access control permissions for the different user.

11. The apparatus of claim 1, wherein the response module is further configured to receive data from one or more sensors of the computing device and the detection module is further configured to base the machine learning analysis at least partially on the received data.

12. The apparatus of claim 11, wherein the one or more sensors comprise an image sensor and the received data comprises one or more images of the user.

13. The apparatus of claim 11, wherein the one or more sensors comprise a touchscreen and the received data comprises touch inputs received from the user during an interactive video game configured to test the user for one or more symptoms of the medical condition.

14. The apparatus of claim 11, wherein the one or more sensors comprise one or more of an accelerometer and a gyroscope and the received data comprises movement information for the computing device by the user.

15. A system comprising:
   a plurality of distributed voice modules disposed and installed on computing devices for a plurality of users, the plurality of distributed voice modules configured to question the plurality of users with one or more open ended questions from one or more of an electronic display screen and a speaker of the computing devices and to record conversational verbal responses from the plurality of users on a microphone of the computing devices, the one or more open ended questions comprising prompts selected from a larger plurality of prompts based on a prompt selection score for each prompt, the prompt selection scores computed using medical diagnoses scores for speech data items of a training corpus; and
   a backend server device configured to store the recorded conversational verbal responses from the plurality of users and machine learning assessments of a medical condition for the recorded conversational verbal responses and to provide the stored recorded conversational verbal responses and machine learning assessments to at least a subset of the plurality of users on the computing devices through the plurality of distributed voice modules.

16. The system of claim 15, wherein the plurality of users comprises participants in a medical trial for the medical condition and the subset of the plurality of users comprises one or more administrators of the medical trial with hierarchical access control permissions to access the stored recorded conversational verbal responses and machine learning assessments.

17. The system of claim 15, wherein the stored recorded conversational verbal responses comprise baseline recorded conversational verbal responses and test case recorded conversational verbal responses and the plurality of distributed voice modules are configured to determine the machine learning assessments on the computing devices based on the baseline recorded conversational verbal responses and the test case recorded conversational verbal responses.

18. The system of claim 15, wherein the stored recorded conversational verbal responses comprise baseline recorded conversational verbal responses and test case recorded conversational verbal responses and the backend server device is configured to determine the machine learning assessments based on the baseline recorded conversational verbal responses and the test case recorded conversational verbal responses.

19. An apparatus comprising:
means for questioning a user from an application installed on a computing device using one or more of an electronic display screen and a speaker of the computing device with one or more open ended questions comprising prompts selected from a larger plurality of prompts based on a prompt selection score for each prompt, the prompt selection scores computed using medical diagnoses scores for speech data items of a training corpus;
means for receiving a conversational verbal response of the user from a microphone of the computing device; and
means for assessing the user for a medical condition using machine learning based on the received conversational verbal response of the user.

20. The apparatus of claim 19, further comprising:
means for authenticating different users in a hierarchy of users; and
means for providing access to different recordings and different assessments to the different users based on hierarchical access control permissions for the hierarchy of users.

* * * * *